United States Patent [19]
Osumi et al.

[11] Patent Number: 6,166,292
[45] Date of Patent: Dec. 26, 2000

[54] RAFFINOSE SYNTHETASE GENE, METHOD OF PRODUCING RAFFINOSE AND TRANSGENIC PLANT

[75] Inventors: Chieko Osumi; Jinshi Nozaki; Takao Kida, all of Kawasaki, Japan

[73] Assignee: Ajinomoto Co., Inc., Tokyo, Japan

[21] Appl. No.: 08/846,234

[22] Filed: Apr. 28, 1997

[30]     Foreign Application Priority Data

Apr. 26, 1996 [JP] Japan .................................. 8-107682
Jul. 26, 1996 [JP] Japan .................................. 8-198079

[51] Int. Cl.$^7$ .............................. C12N 15/82; C12N 5/04; C12N 15/29; A01H 5/00
[52] U.S. Cl. ...................... 800/284; 435/69.1; 435/468; 435/410; 435/419; 435/320.1; 536/23.1; 536/23.2; 536/23.6; 800/278; 800/290; 800/295; 800/298
[58] Field of Search ................................ 536/23.6, 23.1, 536/23.2; 800/278, 284, 290, 295, 298; 435/69.1, 468, 410, 419, 320.1

[56]     References Cited

U.S. PATENT DOCUMENTS

| | | | |
|---|---|---|---|
| 5,346,815 | 9/1994 | Krulwich et al. | 435/69.1 |
| 5,466,595 | 11/1995 | Jones et al. | 435/365 |
| 5,532,152 | 7/1996 | Cousens et al. | 435/197 |
| 5,538,886 | 7/1996 | Schlessinger et al. | 435/425 |
| 5,545,545 | 8/1996 | Gengenbach et al. | 800/278 |
| 5,573,939 | 11/1996 | Båvik et al. | 435/252.33 |
| 5,589,375 | 12/1996 | Ullrich et al. | 435/325 |
| 5,589,385 | 12/1996 | Ryan et al. | 435/252.35 |

FOREIGN PATENT DOCUMENTS

| | | |
|---|---|---|
| WO 93/02196 | 2/1993 | WIPO. |
| WO 93/19190 | 9/1993 | WIPO. |
| WO 98/49273 | 5/1998 | WIPO. |

OTHER PUBLICATIONS

F. Keller et al, "Metabolism of Carbohydrates in Sinks and Sources: Galactosyl–Sucrose Oligosaccharides", Library of Congress Cataloging–in–Publication Data, pp. 157–183.

Ann De Clercq et al, "Stable Accumulation of Modified 2S albumin Seed Storage Proteins with Higher Methionine Contents in Transgenic Plants", Plant Physiol. (1990) 94, pp. 970–979.

C. Lacorte et al, "Transient expression of GUS and 2S albumin gene from Brazil nut in peanut (*Arachis hypogaea* L.) seed explants using particle bombardment", Plant Cell Reports (1997) 16, pp. 619–623.

C. P. Ramono et al, "Uncoupling Auxin and Ethylene Effects in Transgenic Tobacco and Arabidopsis Plants", The Plant Cell, vol. 5, Feb. 1993, pp. 181–189, American Society of Plant Physiologists.

M. W. Lassner et al, "A Jojoba Beta–Ketoacyl–CoA Synthase cDNA Complements the Canola Fatty Acid Elongation Mutation in Transgenic Plants", The Plant Cell, vol. 8, Feb. 1996, pp. 281–292, American Society of Plant Physiologists.

C. Napoli et al, "Introduction of a Chimeric Chalcone Synthase Gene into Petunia Results in Reversible Co–Suppression of Homologous Genes in trans", The Plant Cell, vol. 2, Apr. 1990, pp. 279–289, American Society of Plant Physiologists.

Hiroyuki Hashimoto, et al., Trends in Glycoscience and Glycotechnology, vol. 7, No. 34, pp. 149 to 158, "Synthesis of α–Galactosides with α–Galactosidase from *Candida guilliermondii* H–404", Mar. 1995.

*Primary Examiner*—Lynette R. F. Smith
*Assistant Examiner*—Ousama M-Faiz Zaghmout
*Attorney, Agent, or Firm*—Oblon, Spivak, McClelland, Maier & Neustadt, P.C.

[57]     ABSTRACT

Raffinose synthase purified from cucumber is allowed to act on sucrose and galactinol. Thus raffinose is efficiently produced. The function of endogenous raffinose synthase is regulated by transforming a plant with a chimeric gene comprising a raffinose synthase gene and a regulatory region expressible in the plant. Thus a plant, in which raffinose family oligosaccharides are decreased, is created.

41 Claims, 7 Drawing Sheets

(SEQ ID NO:6) A1 5'– TTY TAY CTB ACH GTN CAY CCT CA –3' (SEQ ID NO:10)
(SEQ ID NO:7) A2 5'– TTY TAY CTB ACH GTN CAY CCC CA –3' B1 5'– GAR GGN GTN MGN CAY CTR GTN GAY GG –3' (SEQ ID NO:11)
(SEQ ID NO:8) A3 5'– TTY TAY CTB ACH GTN CAY CCA CA –3' B2 5'– GAR GGN GTN MGN CAY CTY GTN GAY GG –3' (SEQ ID NO:12)
(SEQ ID NO:9) A4 5'– TTY TAY CTB ACH GTN CAY CCG CA –3' B3 5'– GAR GGN GTN MGN CAY TTR GTN GAY GG –3'

Phe Tyr Leu Thr Val His Pro Gln Gly Val Ile Glu Gly Val Arg His Leu Val Asp Gly Cys
Phe Gly Trp Cys Thr Trp Asp Ala
(SEQ ID NO:1)
                              (SEQ ID NO:18) 3'– CTY CCN CAN KCI GTR GAY CAI CTR CC –5' B'1
                              (SEQ ID NO:19) 3'– CTY CCN CAN KCI GTR GAR CAI CTR CC –5' B'2
                              (SEQ ID NO:20) 3'– CTY CCN CAN KCI GTR TAY CAI CTR CC –5' B'3

D1 5'– TTY GAY GCN TCN GAR CCH GAY TCD CGN CA –3' (SEQ ID NO:15)
D2 5'– TTY GAY GCN TCN GAR CCH GAY TCD CGN CA –3' (SEQ ID NO:16)

C1 5'– GTN GGN TGY TTY GTN GGY TTY GAY GC –3' (SEQ ID NO:13)
C2 5'– GTN GGN TGY TTY GTN GGR TTY GAY GC –3' (SEQ ID NO:14)

Pro Val Ser Val Gly Cys Phe Val Gly Phe Asp Ala Ser Glu Pro Asp Ser Arg His
(SEQ ID NO:2)
                 3'– AAR CTR CGN AGI CTY GGD CTR AGH GCI GT –5' D'1 (SEQ ID NO:21)
                 3'– AAR CTR CGN AGI CTY GGD CTR AGH TCR GTR –5' D'2 (SEQ ID NO:22)

E 5'– GAY CAR GAY CTR ATG GTN GT –3' (SEQ ID NO:17)
Tyr Asp Gln Asp Leu Met Val Val Val Gln Val Pro Trp Pro
(SEQ ID NO:3)

*FIG. 7*

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
       (A) LENGTH: 30 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO:1:

Phe Gly Trp Cys Thr Trp Asp Ala Phe Tyr Leu Thr Val His Pro Gln
 1               5                  10                  15

Gly Val Ile Glu Gly Val Arg His Leu Val Asp Gly Gly Cys
             20                  25                  30

(2) INFORMATION FOR SEQ ID NO:2:

(i) SEQUENCE CHARACTERISTICS:
       (A) LENGTH: 19 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO:2:

Pro Val Ser Val Gly Cys Phe Val Gly Phe Asp Ala Ser Glu Pro Asp
 1               5                  10                  15

Ser Arg His (2) INFORMATION FOR SEQ ID NO:3:

(i) SEQUENCE CHARACTERISTICS:
       (A) LENGTH: 14 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO:3:

Tyr Asp Gln Asp Gln Met Val Val Val Gln Val Pro Trp Pro
 1               5                  10

(2) INFORMATION FOR SEQ ID NO:4:

(i) SEQUENCE CHARACTERISTICS:
       (A) LENGTH: 2517 base pairs
       (B) TYPE: nucleic acid
       (C) STRANDEDNESS: double
       (D) TOPOLOGY: linear (ii) MOLECULE TYPE: cDNA to mRNA (vi) ORIGINAL SOURCE:
       (A) ORGANISM: cucumber (Cucumis sativas)

(ix) FEATURE:
       (A) NAME/KEY: CDS (B) LOCATION: 56..2407

(xi) SEQUENCE DESCRIPTION: SEQ ID NO:4:

| | | | | | | | | | | | | | | | | |
|---|---|---|---|---|---|---|---|---|---|---|---|---|---|---|---|---|
| AAAAAACAAC | CCTTCTTTTA | GTTTTTTGGG | TTTGTTTCTT | CTTTTCTTCT | CACAA ATG | | | | | | | | | | | 58 |
| | | | | | Met | | | | | | | | | | | |
| | | | | | 1 | | | | | | | | | | | |

```
GCT CCT AGT TTT AAA AAT GGT GGC TCC AAC GTA GTT TCA TTT GAT GGC        106
Ala Pro Ser Phe Lys Asn Gly Gly Ser Asn Val Val Ser Phe Asp Gly
            5                  10                  15

TTA AAT GAC ATG TCG TCA CCG TTT GCA ATC GAC GGA TCG GAT TTC ACT        154
Leu Asn Asp Met Ser Ser Pro Phe Ala Ile Asp Gly Ser Asp Phe Thr
        20                  25                  30

GTG AAC GGT CAT TCG TTT CTG TCC GAT GTT CCT GAG AAC ATT GTT GCT        202
Val Asn Gly His Ser Phe Leu Ser Asp Val Pro Glu Asn Ile Val Ala
    35                  40                  45

TCT CCT TCT CCG TAC ACT TCG ATA GAC AAG TCC CCG GTT TCG GTT GGT        250
Ser Pro Ser Pro Tyr Thr Ser Ile Asp Lys Ser Pro Val Ser Val Gly
50                  55                  60                  65

TGC TTT GTT GGA TTC GAC GCG TCG GAA CCT GAT AGC CGA CAT GTT GTT        298
Cys Phe Val Gly Phe Asp Ala Ser Glu Pro Asp Ser Arg His Val Val
                70                  75                  80

TCG ATT GGG AAG CTG AAG GAT ATT CGG TTT ATG AGT ATT TTC AGG TTT        346
Ser Ile Gly Lys Leu Lys Asp Ile Arg Phe Met Ser Ile Phe Arg Phe
            85                  90                  95

AAG GTT TGG TGG ACT ACA CAC TGG GTT GGT CGA AAT GGT GGG GAT CTT        394
Lys Val Trp Trp Thr Thr His Trp Val Gly Arg Asn Gly Gly Asp Leu
        100                 105                 110

GAA TCG GAG ACT CAG ATT GTG ATC CTT GAG AAG TCA GAT TCT GGT CGA        442
Glu Ser Glu Thr Gln Ile Val Ile Leu Glu Lys Ser Asp Ser Gly Arg
    115                 120                 125

CCG TAT GTT TTC CTT CTT CCG ATC GTT GAG GGA CCG TTC CGA ACC TCG        490
Pro Tyr Val Phe Leu Leu Pro Ile Val Glu Gly Pro Phe Arg Thr Ser
130                 135                 140                 145

ATT CAG CCT GGG GAT GAT GAC TTT GTC GAT GTT TGT GTC GAG AGT GGT        538
Ile Gln Pro Gly Asp Asp Asp Phe Val Asp Val Cys Val Glu Ser Gly
                150                 155                 160

TCG TCG AAA GTT GTT GAT GCA TCG TTC CGA AGT ATG TTG TAT CTT CAT        586
Ser Ser Lys Val Val Asp Ala Ser Phe Arg Ser Met Leu Tyr Leu His
            165                 170                 175

GCT GGT GAT GAT CCG TTT GCA CTT GTT AAA GAG GCG ATG AAG ATC GTG        634
Ala Gly Asp Asp Pro Phe Ala Leu Val Lys Glu Ala Met Lys Ile Val
        180                 185                 190

AGG ACC CAT CTT GGA ACT TTT CGC TTG TTG GAG GAG AAG ACT CCA CCA        682
Arg Thr His Leu Gly Thr Phe Arg Leu Leu Glu Glu Lys Thr Pro Pro
    195                 200                 205

GGT ATC GTG GAC AAA TTC GGT TGG TGC ACG TGG GAC GCG TTT TAC CTA        730
Gly Ile Val Asp Lys Phe Gly Trp Cys Thr Trp Asp Ala Phe Tyr Leu
210                 215                 220                 225

ACG GTT CAT CCA CAG GGC GTA ATA GAA GGC GTG AGG CAT CTC GTC GAC        778
Thr Val His Pro Gln Gly Val Ile Glu Gly Val Arg His Leu Val Asp
                230                 235                 240

GGC GGT TGT CCT CCC GGT TTA GTC CTA ATC GAC GAT GGT TGG CAA TCC        826
Gly Gly Cys Pro Pro Gly Leu Val Leu Ile Asp Asp Gly Trp Gln Ser
            245                 250                 255

ATC GGA CAC GAT TCG GAT CCC ATC ACC AAA GAA GGA ATG AAC CAA ACC        874
Ile Gly His Asp Ser Asp Pro Ile Thr Lys Glu Gly Met Asn Gln Thr
        260                 265                 270

GTC GCC GGC GAG CAA ATG CCC TGC CGT CTT TTG AAA TTC CAA GAG AAT        922
Val Ala Gly Glu Gln Met Pro Cys Arg Leu Leu Lys Phe Gln Glu Asn
    275                 280                 285
```

```
TAC AAA TTC CGT GAC TAC GTC AAT CCC AAG GCC ACC GGC CCC CGA GCC      970
Tyr Lys Phe Arg Asp Tyr Val Asn Pro Lys Ala Thr Gly Pro Arg Ala
290             295                 300                 305

GGC CAG AAG GGG ATG AAG GCG TTT ATA GAT GAA CTC AAA GGA GAG TTT     1018
Gly Gln Lys Gly Met Lys Ala Phe Ile Asp Glu Leu Lys Gly Glu Phe
                310                 315                 320

AAG ACT GTG GAG CAT GTT TAT GTT TGG CAT GCT TTG TGT GGA TAT TGG     1066
Lys Thr Val Glu His Val Tyr Val Trp His Ala Leu Cys Gly Tyr Trp
            325                 330                 335

GGT GGC CTT CGC CCG CAG GTG CCT GGC TTG CCT GAG GCA CGT GTG ATT     1114
Gly Gly Leu Arg Pro Gln Val Pro Gly Leu Pro Glu Ala Arg Val Ile
        340                 345                 350

CAG CCA GTG CTT TCA CCA GGG CTG CAG ATG ACG ATG GAG GAT TTG GCG     1162
Gln Pro Val Leu Ser Pro Gly Leu Gln Met Thr Met Glu Asp Leu Ala
355                 360                 365

GTG GAT AAG ATT GTT CTT CAT AAG GTC GGG CTG GTC CCG CCG GAG AAG     1210
Val Asp Lys Ile Val Leu His Lys Val Gly Leu Val Pro Pro Glu Lys
370                 375                 380                 385

GCT GAG GAG ATG TAC GAA GGA CTT CAT GCT CAT TTG GAA AAA GTT GGG     1258
Ala Glu Glu Met Tyr Glu Gly Leu His Ala His Leu Glu Lys Val Gly
                390                 395                 400

ATC GAC GGT GTT AAG ATT GAC GTT ATC CAC CTA TTG GAG ATG TTG TGT     1306
Ile Asp Gly Val Lys Ile Asp Val Ile His Leu Leu Glu Met Leu Cys
            405                 410                 415

GAA GAC TAT GGA GGG AGA GTG GAT TTG GCA AAG GCA TAT TAC AAA GCA     1354
Glu Asp Tyr Gly Gly Arg Val Asp Leu Ala Lys Ala Tyr Tyr Lys Ala
        420                 425                 430

ATG ACC AAA TCA ATA AAT AAA CAT TTT AAA GGA AAT GGA GTC ATT GCA     1402
Met Thr Lys Ser Ile Asn Lys His Phe Lys Gly Asn Gly Val Ile Ala
435                 440                 445

AGT ATG GAA CAT TGT AAC GAC TTC ATG TTC CTT GGC ACG GAA GCT ATC     1450
Ser Met Glu His Cys Asn Asp Phe Met Phe Leu Gly Thr Glu Ala Ile
450                 455                 460                 465

TCT CTT GGT CGT GTT GGT GAT GAC TTT TGG TGC ACG GAC CCC TCT GGT     1498
Ser Leu Gly Arg Val Gly Asp Asp Phe Trp Cys Thr Asp Pro Ser Gly
                470                 475                 480

GAT CCA AAC GGT ACG TTT TGG CTC CAA GGA TGT CAC ATG GTT CAT TGT     1546
Asp Pro Asn Gly Thr Phe Trp Leu Gln Gly Cys His Met Val His Cys
            485                 490                 495

GCC AAC GAC AGC TTG TGG ATG GGG AAC TTC ATC CAC CCT GAC TGG GAT     1594
Ala Asn Asp Ser Leu Trp Met Gly Asn Phe Ile His Pro Asp Trp Asp
        500                 505                 510

ATG TTC CAA TCC ACC CAC CCT TGT GCC GCC TTC CAT GCT GCC TCT CGA     1642
Met Phe Gln Ser Thr His Pro Cys Ala Ala Phe His Ala Ala Ser Arg
515                 520                 525

GCC ATC TCT GGT GGC CCG ATC TAT GTT AGT GAT TCT GTG GGA AAG CAT     1690
Ala Ile Ser Gly Gly Pro Ile Tyr Val Ser Asp Ser Val Gly Lys His
530                 535                 540                 545

AAC TTT GAT CTT CTG AAA AAA CTA GTG CTT CCT GAT GGA TCG ATC CTT     1738
Asn Phe Asp Leu Leu Lys Lys Leu Val Leu Pro Asp Gly Ser Ile Leu
                550                 555                 560

CGA AGT GAG TAC TAT GCA CTC CCG ACT CGC GAT TGT TTG TTT GAA GAC     1786
Arg Ser Glu Tyr Tyr Ala Leu Pro Thr Arg Asp Cys Leu Phe Glu Asp
            565                 570                 575

CCT TTG CAT AAT GGA GAA ACT ATG CTT AAG ATT TGG AAT CTC AAC AAG     1834
Pro Leu His Asn Gly Glu Thr Met Leu Lys Ile Trp Asn Leu Asn Lys
        580                 585                 590

TTC ACT GGA GTG ATT GGT GCA TTC AAC TGC CAA GGA GGA GGA TGG TGT     1882
Phe Thr Gly Val Ile Gly Ala Phe Asn Cys Gln Gly Gly Gly Trp Cys
```

-continued

```
                     595                 600                 605
CGT GAG ACA CGC CGC AAC CAA TGC TTT TCA CAA TAC TCA AAA CGA GTG        1930
Arg Glu Thr Arg Arg Asn Gln Cys Phe Ser Gln Tyr Ser Lys Arg Val
610             615                 620                 625

ACA TCC AAA ACT AAC CCA AAA GAC ATA GAA TGG CAC AGT GGA GAA AAC        1978
Thr Ser Lys Thr Asn Pro Lys Asp Ile Glu Trp His Ser Gly Glu Asn
                630                 635                 640

CCT ATC TCT ATT GAA GGC GTT AAA ACC TTT GCG CTT TAC CTC TAT CAA        2026
Pro Ile Ser Ile Glu Gly Val Lys Thr Phe Ala Leu Tyr Leu Tyr Gln
                    645                 650                 655

GCC AAA AAA CTT ATC CTC TCC AAG CCC TCT CAA GAT CTT GAC ATA GCT        2074
Ala Lys Lys Leu Ile Leu Ser Lys Pro Ser Gln Asp Leu Asp Ile Ala
            660                 665                 670

CTT GAC CCA TTC GAA TTC GAG CTC ATC ACT GTT TCA CCA GTG ACC AAA        2122
Leu Asp Pro Phe Glu Phe Glu Leu Ile Thr Val Ser Pro Val Thr Lys
675                 680                 685

CTC ATC CAA ACT TCT CTA CAC TTT GCC CCA ATT GGG CTG GTG AAC ATG        2170
Leu Ile Gln Thr Ser Leu His Phe Ala Pro Ile Gly Leu Val Asn Met
690                 695                 700                 705

CTT AAC ACT AGT GGA GCC ATC CAA TCT GTG GAC TAT GAC GAT GAC CTA        2218
Leu Asn Thr Ser Gly Ala Ile Gln Ser Val Asp Tyr Asp Asp Asp Leu
                710                 715                 720

AGC TCA GTC GAG ATT GGT GTC AAA GGG TGT GGT GAG ATG CGA GTA TTT        2266
Ser Ser Val Glu Ile Gly Val Lys Gly Cys Gly Glu Met Arg Val Phe
            725                 730                 735

GCA TCG AAA AAA CCA AGG GCT TGT CGT ATT GAT GGG GAG GAT GTT GGG        2314
Ala Ser Lys Lys Pro Arg Ala Cys Arg Ile Asp Gly Glu Asp Val Gly
        740                 745                 750

TTC AAG TAT GAT CAG GAC CAA ATG GTG GTG GTT CAA GTG CCA TGG CCA        2362
Phe Lys Tyr Asp Gln Asp Gln Met Val Val Val Gln Val Pro Trp Pro
755                 760                 765

ATT GAT TCT TCA TCG GGT GGC ATT TCG GTT ATC GAG TAC TTG TTT            2407
Ile Asp Ser Ser Ser Gly Gly Ile Ser Val Ile Glu Tyr Leu Phe
770                 775                 780

TAATTTTTAT TTATGTAAGC TCAATGATTG TTGTTGTTGT CGCTGTTGTT GCTATCAATG      2467

TATTTCTCTC CAAAAGAAAA TTATGTGTAA TTTGGAGAGT AATTAAGTGA                 2517

(2) INFORMATION FOR SEQ ID NO:5:

(i) SEQUENCE CHARACTERISTICS:
        (A) LENGTH: 784 amino acids
        (B) TYPE: amino acid
        (D) TOPOLOGY: linear (ii) MOLECULE TYPE: protein (xi) SEQUENCE DESCRIPTION: SEQ ID NO:5:

Met Ala Pro Ser Phe Lys Asn Gly Gly Ser Asn Val Val Ser Phe Asp
1               5                   10                  15

Gly Leu Asn Asp Met Ser Ser Pro Phe Ala Ile Asp Gly Ser Asp Phe
                20                  25                  30

Thr Val Asn Gly His Ser Phe Leu Ser Asp Val Pro Glu Asn Ile Val
            35                  40                  45

Ala Ser Pro Ser Pro Tyr Thr Ser Ile Asp Lys Ser Pro Val Ser Val
        50                  55                  60

Gly Cys Phe Val Gly Phe Asp Ala Ser Glu Pro Asp Ser Arg His Val
65                  70                  75                  80

Val Ser Ile Gly Lys Leu Lys Asp Ile Arg Phe Met Ser Ile Phe Arg
                85                  90                  95
```

```
Phe Lys Val Trp Trp Thr Thr His Trp Val Gly Arg Asn Gly Gly Asp
            100                 105                 110

Leu Glu Ser Glu Thr Gln Ile Val Ile Leu Glu Lys Ser Asp Ser Gly
            115                 120                 125

Arg Pro Tyr Val Phe Leu Leu Pro Ile Val Glu Gly Pro Phe Arg Thr
            130                 135                 140

Ser Ile Gln Pro Gly Asp Asp Phe Val Asp Val Cys Val Glu Ser
145                 150                 155                 160

Gly Ser Ser Lys Val Val Asp Ala Ser Phe Arg Ser Met Leu Tyr Leu
                165                 170                 175

His Ala Gly Asp Asp Pro Phe Ala Leu Val Lys Glu Ala Met Lys Ile
            180                 185                 190

Val Arg Thr His Leu Gly Thr Phe Arg Leu Leu Glu Glu Lys Thr Pro
            195                 200                 205

Pro Gly Ile Val Asp Lys Phe Gly Trp Cys Thr Trp Asp Ala Phe Tyr
            210                 215                 220

Leu Thr Val His Pro Gln Gly Val Ile Glu Gly Val Arg His Leu Val
225                 230                 235                 240

Asp Gly Gly Cys Pro Pro Gly Leu Val Leu Ile Asp Asp Gly Trp Gln
                245                 250                 255

Ser Ile Gly His Asp Ser Asp Pro Ile Thr Lys Glu Gly Met Asn Gln
            260                 265                 270

Thr Val Ala Gly Glu Gln Met Pro Cys Arg Leu Leu Lys Phe Gln Glu
            275                 280                 285

Asn Tyr Lys Phe Arg Asp Tyr Val Asn Pro Lys Ala Thr Gly Pro Arg
            290                 295                 300

Ala Gly Gln Lys Gly Met Lys Ala Phe Ile Asp Glu Leu Lys Gly Glu
305                 310                 315                 320

Phe Lys Thr Val Glu His Val Tyr Val Trp His Ala Leu Cys Gly Tyr
                325                 330                 335

Trp Gly Gly Leu Arg Pro Gln Val Pro Gly Leu Pro Glu Ala Arg Val
            340                 345                 350

Ile Gln Pro Val Leu Ser Pro Gly Leu Gln Met Thr Met Glu Asp Leu
            355                 360                 365

Ala Val Asp Lys Ile Val Leu His Lys Val Gly Leu Val Pro Pro Glu
370                 375                 380

Lys Ala Glu Glu Met Tyr Glu Gly Leu His Ala His Leu Glu Lys Val
385                 390                 395                 400

Gly Ile Asp Gly Val Lys Ile Asp Val Ile His Leu Leu Glu Met Leu
                405                 410                 415

Cys Glu Asp Tyr Gly Gly Arg Val Asp Leu Ala Lys Ala Tyr Tyr Lys
            420                 425                 430

Ala Met Thr Lys Ser Ile Asn Lys His Phe Lys Gly Asn Gly Val Ile
            435                 440                 445

Ala Ser Met Glu His Cys Asn Asp Phe Met Phe Leu Gly Thr Glu Ala
450                 455                 460

Ile Ser Leu Gly Arg Val Gly Asp Asp Phe Trp Cys Thr Asp Pro Ser
465                 470                 475                 480

Gly Asp Pro Asn Gly Thr Phe Trp Leu Gln Gly Cys His Met Val His
                485                 490                 495

Cys Ala Asn Asp Ser Leu Trp Met Gly Asn Phe Ile His Pro Asp Trp
            500                 505                 510
```

-continued

```
Asp Met Phe Gln Ser Thr His Pro Cys Ala Ala Phe His Ala Ala Ser
        515                 520                 525

Arg Ala Ile Ser Gly Gly Pro Ile Tyr Val Ser Asp Ser Val Gly Lys
    530                 535                 540

His Asn Phe Asp Leu Leu Lys Lys Leu Val Leu Pro Asp Gly Ser Ile
545                 550                 555                 560

Leu Arg Ser Glu Tyr Tyr Ala Leu Pro Thr Arg Asp Cys Leu Phe Glu
                565                 570                 575

Asp Pro Leu His Asn Gly Glu Thr Met Leu Lys Ile Trp Asn Leu Asn
            580                 585                 590

Lys Phe Thr Gly Val Ile Gly Ala Phe Asn Cys Gln Gly Gly Gly Trp
        595                 600                 605

Cys Arg Glu Thr Arg Arg Asn Gln Cys Phe Ser Gln Tyr Ser Lys Arg
    610                 615                 620

Val Thr Ser Lys Thr Asn Pro Lys Asp Ile Glu Trp His Ser Gly Glu
625                 630                 635                 640

Asn Pro Ile Ser Ile Glu Gly Val Lys Thr Phe Ala Leu Tyr Leu Tyr
                645                 650                 655

Gln Ala Lys Lys Leu Ile Leu Ser Lys Pro Ser Gln Asp Leu Asp Ile
            660                 665                 670

Ala Leu Asp Pro Phe Glu Phe Glu Leu Ile Thr Val Ser Pro Val Thr
        675                 680                 685

Lys Leu Ile Gln Thr Ser Leu His Phe Ala Pro Ile Gly Leu Val Asn
    690                 695                 700

Met Leu Asn Thr Ser Gly Ala Ile Gln Ser Val Asp Tyr Asp Asp Asp
705                 710                 715                 720

Leu Ser Ser Val Glu Ile Gly Val Lys Gly Cys Gly Glu Met Arg Val
                725                 730                 735

Phe Ala Ser Lys Lys Pro Arg Ala Cys Arg Ile Asp Gly Glu Asp Val
            740                 745                 750

Gly Phe Lys Tyr Asp Gln Asp Gln Met Val Val Val Gln Val Pro Trp
        755                 760                 765

Pro Ile Asp Ser Ser Ser Gly Gly Ile Ser Val Ile Glu Tyr Leu Phe
    770                 775                 780

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc= "Synthetic DNA"

(xi) SEQUENCE DESCRIPTION: SEQ ID NO:6:

TTYTAYCTBA CHGTNCAYCC TCA                                              23

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc= "Synthetic DNA"
```

(xi) SEQUENCE DESCRIPTION: SEQ ID NO:7:

TTYTAYCTBA CHGTNCAYCC CCA                                    23

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc= "Synthetic DNA"

(xi) SEQUENCE DESCRIPTION: SEQ ID NO:8:

TTYTAYCTBA CHGTNCAYCC ACA                                    23

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc= "Synthetic DNA"

(xi) SEQUENCE DESCRIPTION: SEQ ID NO:9:

TTYTAYCTBA CHGTNCAYCC GCA                                    23

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc= "Synthetic DNA"

(ix) FEATURE:
        (A) NAME/KEY:
        (B) LOCATION:
        (D) OTHER INFORMATION: N at 6 and 11 = inosine
            Other N = A, G, C, or T (xi) SEQUENCE DESCRIPTION: SEQ ID NO:10:

GARGGNGTNM GNCAYCTRGT NGAYGG                                 26

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc= "Synthetic DNA"

(ix) FEATURE:
        (A) NAME/KEY:
        (B) LOCATION:
        (D) OTHER INFORMATION: N at 6 and 11 = inosine
            Other N = A, G, C, or T (xi) SEQUENCE DESCRIPTION: SEQ ID NO:11:

GARGGNGTNM GNCAYCTYGT NGAYGG                                 26

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc= "Synthetic DNA"

(ix) FEATURE:
        (A) NAME/KEY:
        (B) LOCATION:
        (D) OTHER INFORMATION: N at 6 and 11 = inosine
            Other N = A, G, C, or T (xi) SEQUENCE DESCRIPTION: SEQ ID NO:12:

GARGGNGTNM GNCAYTTRGT NGAYGG                                    26

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc= "Synthetic DNA"

(ix) FEATURE:
        (A) NAME/KEY:
        (B) LOCATION:
        (D) OTHER INFORMATION: N at 3 = inosine
            Other N = A, G, C, or T (xi) SEQUENCE DESCRIPTION: SEQ ID NO:13:

GTNGGNTGYT TYGTNGGYTT YGAYGC                                    26

(2) INFORMATION FOR SEQ ID NO:14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc= "Synthetic DNA"

(ix) FEATURE:
        (A) NAME/KEY:
        (B) LOCATION:
        (D) OTHER INFORMATION: N at 3 = inosine
            Other N = A, G, C, or T (xi) SEQUENCE DESCRIPTION: SEQ ID NO:14:

GTNGGNTGYT TYGTNGGRTT YGAYGC                                    26

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc= "Synthetic DNA"

```
    (ix) FEATURE:
        (A) NAME/KEY:
        (B) LOCATION:
        (D) OTHER INFORMATION: N at 9 and 11 = inosine
            Other N = A, G, C, or T (xi) SEQUENCE DESCRIPTION: SEQ ID NO:15:

TTYGAYGCNT CNGARCCHGA YTCDCGNCA                                           29

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc= "Synthetic DNA"

(ix) FEATURE:
        (A) NAME/KEY:
        (B) LOCATION:
        (D) OTHER INFORMATION: N at 9 and 11 = inosine
            Other N = A, G, C, or T (xi) SEQUENCE DESCRIPTION: SEQ ID NO:16:

TTYGAYGCNT CNGARCCHGA YTCDAGYCAY                                          30

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc= "Synthetic DNA"

(xi) SEQUENCE DESCRIPTION: SEQ ID NO:17:

GAYCARGAYC TRATGGTNGT                                                     20

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc= "Synthetic DNA"

(ix) FEATURE:
        (A) NAME/KEY:
        (B) LOCATION:
        (D) OTHER INFORMATION: N at 6 and 15 = inosine
            Other N = A, G, C, or T (xi) SEQUENCE DESCRIPTION: SEQ ID NO:18:

CCRTCNACYA GRTGNCKNAC NCCYTC                                              26

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear
```

```
    (ii) MOLECULE TYPE: other nucleic acid
         (A) DESCRIPTION:    /desc= "Synthetic DNA"

(ix) FEATURE:
         (A) NAME/KEY:
         (B) LOCATION:
         (D) OTHER INFORMATION: N at 6 and 15 = inosine
             Other N = A, G, C, or T (xi) SEQUENCE DESCRIPTION: SEQ ID NO:19:

CCRTCNACRA GRTGNCKNAC NCCYTC                                            26

(2) INFORMATION FOR SEQ ID NO:20:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: other nucleic acid
         (A) DESCRIPTION:    /desc= "Synthetic DNA"

(ix) FEATURE:
         (A) NAME/KEY:
         (B) LOCATION:
         (D) OTHER INFORMATION: N at 6 and 15 = inosine
             Other N = A, G, C, or T (xi) SEQUENCE DESCRIPTION: SEQ ID NO:20:

CCRTCNACYA TRTGNCKNAC NCCYTC                                            26

(2) INFORMATION FOR SEQ ID NO:21:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: other nucleic acid
         (A) DESCRIPTION:    /desc= "Synthetic DNA"

(ix) FEATURE:
         (A) NAME/KEY:
         (B) LOCATION:
         (D) OTHER INFORMATION: N at 3 and 18 = inosine
             Other N = A, G, C, or T (xi) SEQUENCE DESCRIPTION: SEQ ID NO:21:

TGNCGHGART CDGGYTCNGA NGCRTCRAA                                         29

(2) INFORMATION FOR SEQ ID NO:22:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid
         (A) DESCRIPTION:    /desc= "Synthetic DNA"

(ix) FEATURE:
         (A) NAME/KEY:
         (B) LOCATION:
         (D) OTHER INFORMATION: N at 19 = inosine
             Other N = A, G, C, or T (xi) SEQUENCE DESCRIPTION: SEQ ID NO:22:

RTGRCTHGAR TCDGGYTCNG ANGCRTCRAA                                        30
```

RAFFINOSE SYNTHETASE GENE, METHOD OF PRODUCING RAFFINOSE AND TRANSGENIC PLANT

TECHNICAL FIELD

The present invention relates to a raffinose synthase, a method for raffinose synthesis based on the use of raffinose synthase or a cell-free extract containing the raffinose synthase, DNA coding for the raffinose synthase, and methods for its use to produce altered amount of raffinose family oligosaccharides in transformed plants. Raffinose is utilized in a variety of fields, as a food material having an activity to proliferate Bifidzbacterium, or as a pharmaceutical to be used, for example, for solutions of organ preservation.

BACKGROUND ART

Raffinose is one of raffinose family oligosaccharides, in which galactose is connected to glucosyl group of sucrose via α-1,6 linkage. The raffinose family oligosaccharides include, for example, stachyose containing two connected galactose residues, and verbascose containing three connected galactose residues, in addition to raffinose. These oligosaccharides are widely distributed in plants, for example, seeds of various plants such as beans, rapeseed, and cottonseed containing these oligosaccharides as reserve carbohydrates; plants belonging to Cucurbitaceae such as cucumber and melon containing these sugars as transport sugars; and sugar beet (*Beta vulgaris*) and rosette leaves having acquired cold resistance.

The raffinose family oligosaccharides are biosynthesized as follows.

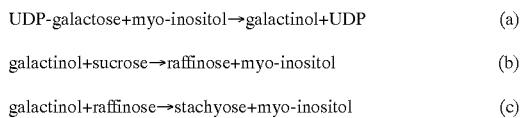

UDP-galactose+myo-inositol→galactinol+UDP  (a)

galactinol+sucrose→raffinose+myo-inositol  (b)

galactinol+raffinose→stachyose+myo-inositol  (c)

The respective reactions are catalyzed by (a) galactinol synthase (GS: EC 2.4.1.123), (b) raffinose synthase (RS: EC 2.4.1.82), and (c) stachyose synthase (STS: EC 2.4.1.67).

At present, raffinose is extracted from sugar beet, and it is separated and purified in the sucrose purification process. However, since crystal formation of sucrose is deteriorated by raffinose, sugar beet has been subjected to breeding and improvement with the aim of decreasing the raffinose content. As a result, the raffinose content in sugar beet now has a low value of 0.03% to 0.16% (*Enzyme Microb. Technol.*, Vol. 4, May, 130–135 (1982)). Therefore, it is not easy to efficiently obtain raffinose from sugar beet having such a low raffinose content.

As described above, raffinose is contained in mature seeds of plants belonging to Lequminosae represented by soybean. Mature seed of soybean contains, as soybean oligosaccharides, sucrose (content: about 5%), stachyose (content: about 4%), and raffinose (content: about 1%). The soybean oligosaccharides are recovered in a fraction obtained by deproteinizing defatted soybean, and they are utilized, for example, for functional food products after concentration. However, raffinose occupies a proportion of 10% of the whole oligosaccharides, and hence raffinose exists in a small amount.

On the other hand, a method for enzymatically synthesizing raffinose has been reported (*Trends in Glycoscience and Glycotechnology*, 7.34, 149–158 (1995)). This method comprises the steps of synthesizing galactobiose in accordance with a condensation reaction catalyzed by α-galactosidase, and transferring galactosyl group to sucrose by using the galactobiose as a galactosyl group donor in accordance with a galactosyl transfer reaction to synthesize raffinose. However, in this reaction, 350 g of galactobiose is synthesized from 1.9 kg of lactose hydrolysate, and 100 g of raffinose is obtained from 190 g of galactobiose and 760 g of sucrose. Therefore, the yield of produced raffinose is low, and hence this synthesis method is not efficient.

Besides the foregoing methods, a method is also conceivable in which a plant having a high raffinose content may be bred by means of transformation for genes for enzymes included in the biosynthesis system. For example, Kerr et al. have cloned a gene for galactinol synthase, and transformed rapeseed therewith (WO 93/02196). As a result, the GS activity was increased, however, the content of the raffinose family oligosaccharides was unwillingly decreased. It was impossible to achieve the object to enhance the biosynthesis of the raffinose family oligosaccharides by transforming the galactinol synthase gene. Therefore, there has not been provided a method for increasing the content of the raffinose family oligosaccharides in plant.

On the other hand, it is also demanded to decrease the raffinose family oligosaccharides. As described above, the raffinose family oligosaccharides are widely distributed over plants including, seeds of various plants such as beans, for example, soybean, rapeseed, and cottonseed containing these oligosaccharides as storage carbohydrates; plants belonging to Cucurbitaceae such as cucumber and melon containing these oligosaccharides as transport sugars; and sugar beet and rosette leaves having acquired cold resistance. Meals obtained after extraction of oil, for example, from soybean, rapeseed, and cotton contain the raffinose family oligosaccharides. Almost all of the meals are utilized as feed. However, human and animals, which do not have α-galactosidase, cannot directly digest the raffinose family oligosaccharides. It is known that the raffinose family oligosaccharides lower the metabolic energy efficiency of feed due to, for example, assimilation of the raffinose family oligosaccharides by enteric bacteria to cause gas production. It has been reported that removal of raffinose family oligosaccharides from soybean meal results in a large increase in the metabolizable energy for broiler chickens (Coon, "Proceeding Soybean Utilization Alternatives", Univrsity of Minnesota, 203–211 (1989)). In view of the foregoing facts, it is desired to develop the plants such as soybean, rapeseed, and cottonseed in which the raffinose family oligosaccharides are decreased.

Such plants have been subjected to breeding to increase the amount of oil. Photosynthetic products are distributed over oils, proteins, and carbohydrates including the raffinose family oligosaccharides. It has been reported for soybean that a reverse correlation exists between the amount of oils and the amount of carbohydrates. It is expected that the content of oils can be increased in a soybean plant having the same photosynthetic ability as those possessed by others, by decreasing the production of the raffinose family oligosaccharides.

Based on a viewpoint as described above, Kerr et al. have reported development of soybean varieties with a low content of the raffinose family oligosaccharides, by means of breeding based on mating and selection, in which the raffinose family oligosaccharides are lowered by an amount of 80% to 90% (WO 93/00742). However, this technique concerns creation of soybean variety, which cannot be applied to other various soybean varieties developed in response to, for example, aptitude for cultivation and resistance to disease. This technique cannot be universally applied to various plants as well.

It is known that raffinose, which is contained, for example, in sugar beet and sugar cane, lowers crystal formation of sugar or sucrose. Therefore, it is possible to expect that if no raffinose is produced, the production efficiency of sugar may be improved in such a plant. However, no sugar beet has been created, which contains no raffinose.

As described above, the raffinose synthase, which has been hitherto purified, has been confirmed only as an enzyme activity, and no entity of the enzyme has been identified. The confirmed activity is low, and it has been desired to obtain a raffinose synthase having a high activity. The conventional method for producing raffinose provides a low yield, and hence it has been desired to develop an efficient method for producing raffinose. On the other hand, it is also desired to breed a plant in which the raffinose family oligosaccharides are decreased.

DISCLOSURE OF THE INVENTION

The present invention has been made taking the foregoing viewpoints into consideration, an object of which is to obtain a raffinose synthase having a high activity and DNA encoding raffinose synthase, and provide an efficient method for enzymatically synthesis raffinose, and a method for utilizing DNA encoding raffinose synthase in plants.

As a result of diligent investigations in order to achieve the object described above, the present inventors have succeeded in purifying a raffinose synthase from cucumber. Further diligent investigations have been made by the present inventors in order to clone a gene coding for the raffinose synthase. As a result, a DNA fragment specific to a gene for the raffinose synthase has been obtained by chemically synthesizing single strand DNA's on the basis of nucleotide sequences deduced from amino acid sequences of peptide fragments of the cucumber raffinose synthase, and performing PCR by using the single strand synthetic DNA's as primers and using cDNA's prepared from poly(A)$^+$RNA extracted from cucumber as templates. Further, the raffinose synthase gene has been isolated by adopting a method in which hybridization is performed for a cDNA library originating from cucumber by using the DNA fragment as a probe. A chimeric gene having a regulatory region expressible in plants has been prepared by using a fragment of the isolated raffinose synthase gene to transform a plant. Further, the function of endogenous raffinose synthase has been regulated by introducing the raffinose synthase gene to create a plant in which the raffinose family oligosaccharides are decreased.

Namely, the present invention provides a raffinose synthase which has the following properties:

(1) action and substrate specificity: the raffinose synthase produces raffinose from sucrose and galactinol;

(2) optimum pH: the raffinose synthase has an optimum pH of about 6 to 8;

(3) optimum temperature: the raffinose synthase has an optimum temperature of about 35 to 40° C.;

(4) molecular weight: the raffinose synthase has:
 (i) a molecular weight of about 75 kDa to 95 kDa estimated by gel filtration chromatography;
 (ii) a molecular weight of about 90 kDa to 100 kDa estimated by polyacrylamide gel electrophoresis (Native PAGE); and
 (iii) a molecular weight of about 90 kDa to 100 kDa estimated by SDS-polyacrylamide gel electrophoresis (SDS-PAGE) under a reduced condition;

(5) inhibition: the raffinose synthase is inhibited by iodoacetamide, N-ethylmaleimide, and myo-inositol.

In a specified embodiment of the foregoing raffinose synthase provided by the present invention, the raffinose synthase has an amino acid sequence including respective amino acid sequences shown in SEQ ID NOs. 1 to 3 in Sequence Listing.

In another aspect of the present invention, there is provided a raffinose synthase which is a protein specified by the following item (A) or (B):

(A) a protein which has an amino acid sequence shown in SEQ ID NO: 5 in Sequence Listing; or (B) a protein which comprises an amino acid sequence including substitution, deletion, insertion, addition, or inversion of one or several residues of amino acids in the amino acid sequence shown in SEQ ID NO: 5 in Sequence Listing, and which has an activity to produce raffinose from sucrose and galactinol.

In still another aspect of the present invention, there is provided a method for producing raffinose, comprising the step of allowing the foregoing raffinose synthase to act on sucrose and galactinol to produce raffinose.

In still another aspect of the present invention, there are provided DNA encoding raffinose synthase, and DNA coding for a protein specified by the following item (A) or (B):

(A) a protein which has an amino acid sequence shown in SEQ ID NO: 5 in Sequence Listing; or (B) a protein which comprises an amino acid sequence including substitution, deletion, insertion, addition, or inversion of one or several residues of amino acids in the amino acid sequence shown in SEQ ID NO: 5 in Sequence Listing, and which has an activity to produce raffinose from sucrose and galactinol.

In a specified embodiment of the foregoing DNA of the present invention, there is provided DNA specified by the following item (a) or (b):

(a) DNA which includes a nucleotide sequence comprising at least nucleotide residues having nucleotide numbers of 57 to 2408 in a nucleotide sequence shown in SEQ ID NO: 4 in Sequence Listing; or (b) DNA which is hybridizable under a stringent condition with the nucleotide sequence comprising at least nucleotide residues having nucleotide numbers of 57 to 2408 in the nucleotide sequence shown in SEQ ID NO: 4 in Sequence Listing, and which codes for a protein having an activity to produce raffinose from sucrose and galactinol.

In still another aspect of the present invention, there are provided a chimeric gene comprising a raffinose synthase gene or a part thereof, and a transcription regulatory region expressible in plant cells, and a plant transformed with the chimeric gene.

In still another aspect of the present invention, there is provided a method for changing a content of raffinose family oligosaccharides in a plant, comprising the steps of transforming the plant with the chimeric gene, and expressing the gene in the plant.

In the following description, the raffinose synthase having the properties described in the foregoing items (1) to (5), or the raffinose synthase specified as the protein defined in the foregoing items (A) and (B) is simply referred to as "raffinose synthase" in some cases. DNA encoding raffinose synthase, or DNA encoding raffinose synthase and including non-translating regions is referred to as "raffinose synthase gene" in some cases.

The present invention will be explained in detail below.

<1> Raffinose Synthase of the Present Invention

The raffinose synthase of the present invention has the following properties:

(1) action and substrate specificity: the raffinose synthase produces raffinose from sucrose and galactinol;

(2) optimum pH: the raffinose synthase has an optimum pH of about 6 to 8;

(3) optimum temperature: the raffinose synthase has an optimum temperature of about 35 to 40° C.;

(4) molecular weight: the raffinose synthase has:
  (i) a molecular weight of about 75 kDa to 95 kDa estimated by gel filtration chromatography;
  (ii) a molecular weight of about 90 kDa to 100 kDa estimated by polyacrylamide gel electrophoresis (Native PAGE); and
  (iii) a molecular weight of about 90 kDa to 100 kDa estimated by SDS-polyacrylamide gel electrophoresis (SDS-PAGE) under a reduced condition;

(5) inhibition: the raffinose synthase is inhibited by iodoacetamide, N-ethylmaleimide, and myo-inositol.

The raffinose synthase having the foregoing properties has been isolated and purified from leaves of cucumber, which has been identified for the first time by the present inventors. As demonstrated in Examples described later on, the raffinose synthase originating from cucumber includes the respective amino acid residues shown in SEQ ID NOs: 1 to 3 in Sequence Listing, in the amino acid sequence of the enzyme protein. An entire amino acid sequence of the raffinose synthase is shown in SEQ ID NO: 5.

The raffinose synthase is obtainable from plants belonging to Cucurbitaceae, for example, plants such as melon (*Cucumis melo*) and cucumber (*Cucumis sativus*). Especially, the raffinose synthase is contained in a large amount in leaves of these plants, especially in tissues of leaf veins and seeds.

Next, the method for producing the raffinose synthase of the present invention will be explained in accordance with an illustrative method for isolating and purifying the raffinose synthase from cucumber.

Leaf vein tissues are collected from leaves of cucumber obtained 6 to 10 weeks after planting. The vein are ground by a mortar with liquid nitrogen, to which a buffer is added to extract proteins. During this process, it is allowable to add a substance to prevent the raffinose synthase from degradation and inactivation, for example, a protease inhibitor such as PMSF (phenylmethanesulfonyl fluoride), or polyclarl AT (produced by Serva). Insoluble matters are removed from an obtained extract solution by means of filtration and centrifugation to obtain a crude extract solution.

The crude extract solution thus obtained is subjected to fractionation based on combination of ordinary methods for purifying proteins, including, for example, anion exchange chromatography, hydroxyapatite chromatography, gel filtration, and salting out. Thus the raffinose synthase can be purified.

Anion exchange chromatography can be performed, for example, by using a column charged with a strongly basic anion exchanger such as HiTrap Q (produced by Pharmacia), or a weakly basic anion exchanger such as DEAE-TOYOPEARL (produced by Toyo Soda). The extract solution containing the raffinose synthase is allowed to pass through the column so that the enzyme is adsorbed to the column. After washing the column, the enzyme is eluted by using a buffer having a high salt concentration. During this process, the salt concentration may be increased in a stepwise manner, or the concentration gradient may be applied. For example, when the HiTrap Q column is used, the raffinose synthase activity adsorbed to the column is eluted by NaCl at about 0.3 M. An eluting solution to give an NaCl concentration gradient of 0.05 M to 0.35 M is preferably used for DEAE-TOYOPEARL. An eluting solution to give a phosphate concentration gradient of 0.01 M to 0.3 M is preferably used for hydroxyapatite chromatography.

The order of the foregoing operations is not specifically limited. Each of the operations may be repeated two or more times. It is desirable to exchange a sample solution with an appropriate buffer by means of dialysis or the like before the sample solution is allowed to pass through each column. The sample solution may be concentrated at each stage.

At each stage of the purification, it is preferable that the raffinose synthase activity contained in each of fractionated fractions is measured so that fractions having high activities are collected to be used in the next stage. The method for measuring the raffinose synthase activity is exemplified by a method based on the use of radioisotope as reported, for example, by Lehle, H. et al. (*Eur. J. Biochem.*, 38, 103–110 (1973)). As a modified method thereof, the reaction temperature and the substrate concentration may be changed. For example, 10 $\mu$l of an enzyme solution is added to a reaction solution containing, at final concentrations, 10 mM $^{14}$C-sucrose, 20 mM galactinol, 25 mM HEPES (2-(4-(2-hydroxyethyl)-1-piperazinyl)ethanesulfonic acid)-NaOH, pH 7.0, 0.5 mM DTT (dithiothreitol) to give a volume of 50 $\mu$l. The solution is incubated at 32° C. for 1 hour to perform the reaction. The reaction is stopped by adding 200 $\mu$l of ethanol and heating the solution at 95° C. for 30 seconds. The reaction solution is centrifuged to obtain a supernatant. An aliquot of the supernatant is spotted on Whatman 3MM filter paper, and developed with n-propanol: ethyl acetate: water=4:1:2. Incorporation of $^{14}$C into raffinose is investigated, which is regarded to be the raffinose synthase activity (nmol/hour).

The present inventors have developed a method for measuring the raffinose synthase activity in place of the foregoing method. Namely, the raffinose synthase activity is measured by quantitatively determining raffinose produced by the raffinose synthesis reaction, by means of HPLC (high-performance liquid chromatography). According to this method, the activity can be measured conveniently and quickly as compared with the method of Lehle, H. et al. This method is especially preferable to detect active fractions during the purification operation. This method will be explained below.

The raffinose synthesis reaction is based on the use of a reaction solution prepared to have a composition having the following final concentrations. The reaction solution is added with 10 to 50 $\mu$l of a raffinose synthase solution to give a volume of 100 $\mu$l, followed by performing the reaction at 32° C. for 60 minutes.

[Composition of reaction solution (final concentration)]

2.5 mM sucrose 5 mM galactinol 5 mM DTT 20 mM Tris-HCl buffer (pH 7.0)

After performing the reaction as described above, the reaction solution is added with ethanol in a volume four times the volume of the reaction solution to stop the reaction by heating the solution at 95° C. for 30 seconds. The obtained solution is centrifuged to obtain a supernatant which is then dried up under a reduced pressure. After that, an obtained residue is dissolved in distilled water. Raffinose in the reaction product is quantitatively determined by using HPLC to estimate the raffinose synthase activity. HPLC can be performed by using, for example, Sugar Analysis System DX500 (CarboPac PA1 column, pulsed amperometry detector (produced by Dionecs)).

FIG. 1 shows a result of measurement performed in accordance with the method described above, for the amount of raffinose produced when the reaction time was changed. As clarified from FIG. 1, this method makes it possible to conveniently measure the raffinose synthase activity with excellent linearity.

The degree of purification of the purified raffinose synthase can be confirmed, and the molecular weight can be measured, by means of, for example, gel electrophoresis and gel filtration chromatography. Enzymatic properties can be investigated by measuring the enzyme activity while changing the reaction temperature or the reaction pH, or by measuring the remaining enzyme activity after adding, to the reaction solution, various enzyme inhibitors, metal ions or the like. The stable pH range and the stable temperature range can be investigated by measuring the enzyme activity after exposing the raffinose synthase to various pH conditions and temperature conditions for a certain period of time respectively.

The properties of the raffinose synthase described above have been determined in accordance with procedures as described above. However, it should be noted that different results may be obtained depending on measurement conditions. For example, the measurement for the molecular weight based on the use of gel filtration chromatography is affected by the type of the gel filtration agent and the buffer, and the molecular weight marker to be used. The enzyme activity differs depending on the type of the buffer and the salt concentration in many cases even when the measurement is performed at an identical pH. Therefore, upon identification for the raffinose synthase, it is preferable to perform comprehensive investigation without being bound to only measurement for individual properties.

The raffinose synthase of the present invention is obtained by performing the isolation and purification from cucumber as described above. Alternatively, the raffinose synthase of the present invention can be produced by introducing, into an appropriate host, DNA coding for the raffinose synthase described later on, and making expression thereof, in accordance with ordinary methods used for fermentative production of heterogeneous proteins.

Those assumed as the host for expressing the raffinose synthase gene include various procaryotic cells represented by *Escherichia coli,* and various eucaryotic cells represented by *Saccharomyces cerevisiae.* However, it is desirable to use plant cells, especially cells originating from plants such as tobacco, cucumber, and *Arabidopsis thaliana.*

The recombinant plasmid used for transformation can be prepared by inserting DNA coding for the raffinose synthase into an expression vector in conformity with the type of cells to be used for expression therein. Those usable as the plant expression vector include those having a promoter DNA sequence capable of being expressed in the plant or a combination of a plurality of such promoter DNA sequences, and a terminator DNA sequence workable in the plant, and further having a sequence between the both to make it possible to insert a foreign gene.

The promoter includes, for example, promoters which make expression over a whole plant, such as CaMV 35S RNA promoter, CaMV 19S RNA promoter, and nopaline synthase promoter; promoters which make expression in green tissues, such as Rubisco small subunit promoter; and promoters which make site-specific expression at portions such as seed, including, for example, those for genes of napin and phaseolin. The terminator described above includes, for example, nopaline synthase terminator, and Rubisco small subunit 3'-side portion.

As for the expression vector for plants, for example, pBI121 and p35S-GFP (produced by CLONTECH) are commercially available, which may be used. Alternatively, a vector for expressing virus RNA may be used so that a gene for an outer coat protein encoded thereby, for example, may be replaced with the raffinose synthase gene.

In order to achieve transformation, it is advantageous to use methods which are usually used for transformation, such as the Agrobacterium method, the particle gun method, the electroporation method, and the PEG method, in conformity with a host cell to be manipulated. The raffinose synthase activity can be detected by using the method adopted in the purification process for the raffinose synthase. Upon the detection, it is desirable to previously remove α-galactosidase, for example, by allowing the sample to pass through an anion exchange column.

The gene coding for the raffinose synthase originating from cucumber includes all of those which provide the raffinose synthase activity upon expression. Preferably, the gene is exemplified by the gene comprising DNA coding for the amino acid sequence shown in SEQ ID NO: 5 in Sequence Listing, and the gene having the nucleotide sequence shown in SEQ ID NO: 4 in Sequence Listing. It is noted that the gene coding for the amino acid sequence shown in SEQ ID NO: 5 in Sequence Listing includes various nucleotide sequences taking degeneracy of codons into consideration. Namely, the gene coding for the amino acid sequence shown in SEQ ID NO: 5 in Sequence Listing may be selected from such various nucleotide sequences, while considering several factors for the gene expression system, such as preferential codons depending on, for example, the type of the host cell, and avoidance of higher-order structure to be formed by transcribed RNA. The selected nucleotide sequence may be DNA cloned from the nature, or DNA chemically synthesized in an artificial manner.

<2> DNA Coding for Raffinose Synthase of the Present Invention

DNA coding for the raffinose synthase can be obtained by preparing a cDNA library from poly(A)$^+$RNA isolated from a plant such as cucumber, and screening the cDNA library by means of hybridization. A probe to be used for the hybridization can be obtained by performing amplification by means of PCR (polymerase chain reaction) by using, as primers, oligonucleotides synthesized on the basis of partial amino acid sequences of the raffinose synthase protein.

A method for obtaining DNA of the present invention from poly(A)$^+$RNA originating from cucumber will be specifically explained below.

As for the position for extractiing poly(A)$^+$RNA, all portions of a cucumber plant body may be used provided that the raffinose synthase gene is expressed at that portion. Poly(A)+RNA can be obtained, for example, from leaves, stalks, buds, fruits, and seeds at various growth stages. However, poly(A)$^+$RNA is desirably obtained from a material of fully expanded leaves after fruiting, especially leaf vein portions.

In order to extract total RNA from the cucumber tissue, any method may be used without limitation provided that RNA can be efficiently obtained with less damage. It is possible to use any known method such as the phenol/SDS method and the guanidine isothiocyanate/cesium chloride method. Poly(A)$^+$RNA can be isolated from the total RNA thus obtained, by using an oligo(dT) cellulose. It is also preferable to use a kit (for example, MPG Direct mRNA Purification Kit, produced by CPG, INC.) which makes it possible to obtain poly(A)$^+$RNA without extracting the total RNA.

A DNA fragment, which is used as a probe for screening for the cDNA library, can be obtained by performing PCR. Oligonucleotides, which have nucleotide sequences deduced from already known amino acid sequences of peptide fragments, for example, nucleotide sequences deduced from amino acid sequences shown in SEQ ID NOs: 1 to 3, are chemically synthesized. The obtained oligonucleotides are used as primers to perform PCR. Any portion of the amino acid sequence of the obtained peptide fragment may be used for the primers. However, it is desirable to select sequences which include less degeneracy of codons and which are assumed to form no complicated higher-order structure. Alternatively, it is also preferable to perform RACE (Rapid Amplification of cDNA End, "PCR PROTOCOLS A Guide to Methods and Applications", ACADEMIC press INC., pp. 28 to 38).

It is desirable to use, as a template for PCR, a cDNA library or single strand cDNA. When heat-resistant DNA polymerase having a reverse transcriptase activity is used for the PCR reaction, it is allowable to use poly(A)$^+$RNA, or total RNA in some cases.

In order to prepare the cDNA library, at first single strand cDNA's are synthesized by using reverse transcriptase while using poly(A)$^+$RNA as a template and using oligo(dT) primer and random primers. Next, double strand cDNA's are synthesized in accordance with, for example, the Gubler and Hoffman method, the Okayama-Berg method ("Molecular Cloning", 2nd edition, Cold Spring Harbor press, 1989). When the raffinose synthase gene is expressed in a small amount, cDNA's may be amplified by means of PCR by using a cDNA library construction kit based on the use of PCR (for example, Capfinder PCR cDNA Library Construction Kit (produced by CLONTECH)). cDNA's thus synthesized can be cloned into a cloning vector such as phage vectors and plasmids, after performing, for example, blunt end formation, addition of linker, addition of restriction enzyme site by means of PCR.

A portion characteristic of the raffinose synthase cDNA is selected from the DNA fragments obtained by PCR described above, for the probe for hybridization. It is desirable to select a DNA fragment located near to the 5'-terminal side. The amplified DNA fragment thus selected is purified from a reaction solution of PCR. In this procedure, the amplified DNA fragment may be purified by subcloning the DNA fragment by using a plasmid, preparing a large amount of a subcloned plasmid which is thereafter digested with a restriction enzyme, and excising the DNA fragment from a gel after electrophoresis. Alternatively, the amplified DNA fragment may be purified by performing PCR by using the plasmid as a template to amplify and use only the objective portion. When the amount of the initially amplified DNA fragment is sufficiently large, the amplified DNA fragment may be purified by electrophoresing the DNA fragment without performing subcloning, excising a gel segment containing a band of the objective DNA fragment, and purifying the DNA fragment from the gel segment.

Screening to obtain the objective clone from the cDNA library is performed by means of hybridization. The DNA fragment obtained in accordance with the foregoing method can be labeled and used as a probe for the hybridization. Upon labeling, it is possible to use various labels such as radioisotope and biotin. However, labeling is desirably performed in accordance with the random priming method. Screening may be performed by using PCR instead of hybridization. Further, screening may be performed by using hybridization and PCR in combination.

The nucleotide sequence of DNA coding for the raffinose synthase originating from cucumber obtained as described above, and the amino acid sequence deduced from the nucleotide sequence are illustratively shown in SEQ ID NO: 4 in Sequence Listing. Only the amino acid sequence is shown in SEQ ID NO: 5. A transformant AJ13263 of *Escherichia coli* JM109, which harbors a plasmid pMoss-loxCRS containing the DNA fragment including DNA coding for the raffinose synthase obtained in Example 3 described later on, has been internationally deposited on the basis of the Budapest Treaty since Nov. 19, 1996 in National Institute of Bioscience and Human Technology of Agency of Industrial Science and Technology of Ministry of International Trade and Industry (postal code: 305, 1-3 Higashi-Icchome, Tsukuba-shi, Ibaraki-ken, Japan), and awarded a deposition number of FERM BP-5748.

The DNA of the present invention may code for a raffinose synthase protein including substitution, deletion, insertion, addition, or inversion of one or several residues of amino acids at one or several positions, provided that the activity of raffinose synthase encoded thereby, i.e., the activity to produce raffinose from sucrose and galactinol is not deteriorated. In this context, the number of "several residues" differs depending on the position and the type of the amino acid residues in the three-dimensional structure of the protein, originally because of the following reason. Namely, high similarity is found between some amino acids and other amino acids, for example, between isoleucine and valine, and such a difference in amino acid does not greatly affect the three-dimensional structure of the protein. Therefore, the DNA of the present invention may code for those having homology of not less than 35 to 40% with respect to the entire 784 amino acid residues for constructing the raffinose synthase originating from cucumber, provided that they have the raffinose synthase activity. Preferably, those encoded by the DNA of the present invention have homology of 65% in a region between 510th amino acid and 610th amino acid. Specifically, the number of "several residues" is 2 to 40, preferably 2 to 20, and more preferably 2 to 10.

The present invention includes genes in which homology of not less than about 50% is given for the entire length of the gene, and homology of not less than 65% is given over a region comprising about 300 nucleotide residues. Nucleotide sequence information on such genes can be obtained by searching genes having homology to the raffinose synthase gene originating from cucumber, by using data base such as GenBank. For example, GENETIX-MAC (software for processing genetic information, produced by Software Development), which adopts the Lipman-Person method, may be used as a program for homology analysis. Alternatively, those open to the public on the Internet may be used for this purpose. Some nucleotides sequences obtained by the method as described above contain the entire length of the gene, and other nucleotide sequences do not contain the entire length of the gene. When the entire length of the gene is not contained, the entire length gene can be easily obtained by using RNA extracted from an objective plant tissue as a template, and using primers corresponding to portions having high homology to the raffinose synthase gene originating from cucumber, in accordance with the 5'-RACE method and the 3'-RACE method. The obtained entire length gene may be incorporated into an appropriate expression vector provided as those included in a kit such as Soluble Protein Expression System (produced by INVITROGEN), Tight Control Expression System (produced by INVITROGEN), and QIAexpress System (produced by QIAGEN) so that the gene may be expressed. The raffinose synthase activity may be measured in accordance with the method described above to select a clone having the activity.

DNA, which codes for substantially the same protein as the raffinose synthase, is obtained by modifying the nucleotide sequence in accordance with, for example, the site-directed mutagenesis method so that amino acids located at specified positions are subjected to substitution, deletion, insertion, or addition. Modified DAN as described above may be also obtained in accordance with the conventionally known mutation treatment. The mutation treatment includes a method in which the DNA coding for the raffinose synthase is treated with hydroxylamine or the like in vitro, and a method in which a bacterium belonging to the genus Escherichia harboring the DNA coding for the raffinose synthase gene is treated with ultraviolet irradiation or a mutating agent usually used for artificial mutation, such as nitrous acid and N-methyl-N'-nitro-N-nitrosoguanidine (NTG).

The substitution, deletion, insertion, addition, or inversion of the nucleotide includes mutation which naturally occurs, for example, based on the difference between individuals of a cucumber plant, the difference between varieties, the formation of multiple copies of the gene, the difference between respective organs, and the difference between respective tissues.

DNA having mutation as described above is expressed in an appropriate cell to investigate the raffinose synthase activity of an expressed product. Thus it is possible to obtain DNA which codes for substantially the same protein as the raffinose synthase. Further, DNA coding for substantially the same protein as the raffinose synthase protein can be obtained by isolating DNA which is hybridizable under a stringent condition with DNA having a nucleotide sequence comprising nucleotide residues having, for example, nucleotide numbers of 56 to 2407 in the nucleotide sequence shown in SEQ ID NO: 4 in Sequence Listing, and which codes for the protein having the raffinose synthase activity, from DNA's coding for raffinose synthases having mutation or from cells harboring the DNA's. The phrase "stringent condition" referred to herein indicates a condition in which so-called specific hybrid is formed, and nonspecific hybrid is not formed. It is difficult to definitely express this condition by using numerical values. However, for example, this condition includes a condition in which DNA's having high homology, for example, DNA's having homology of not less than 50% hybridize with each other, while DNA's having homology lower than the above do not hybridize with each other, or a condition in which hybridization is achieved at a salt concentration corresponding to a washing condition for ordinary Southern hybridization, i.e., 1×SSC, 0.1% SDS, and preferably 0.1×SSC, 0.1% SDS at 60° C. Genes, which hybridize under such a condition, include those which contain a stop codon generated at an intermediate position, and those which have lost the activity due to mutation at the active center. However, those having such inconvenient mutation can be easily eliminated by ligating the gene with a commercially available activity expression vector to measure the raffinose synthase activity in accordance with the method described above.

When the DNA of the present invention is used to express antisense RNA for the raffinose synthase, it is unnecessary for the DNA to code for any active raffinose synthase. Further, the function of any endogenous gene having homology can be restrained by using sense RNA. In such a case, it is also unnecessary for the DNA to code for any active raffinose synthase. Further, it is unnecessary for the DNA to contain the entire length. Preferably, it is sufficient for the DNA to have about 500 base pairs of an N-terminal side translating region having 60% of homology.

The method has been explained above, in accordance with which the present inventors have succeeded in cloning the objective cDNA of the raffinose synthase originating from cucumber. However, other than the foregoing, the following methods may be available.

(1) The raffinose synthase originating from cucumber is isolated and purified, and an entire nucleotide sequence is chemically synthesized on the basis of a determined amino acid sequence or the amino acid sequence shown in SEQ ID NO: 5.

(2) Chromosomal DNA is prepared from a cucumber plant body, and a chromosomal DNA library is prepared by using a plasmid vector or the like. The raffinose synthase gene is obtained from the library by means of hybridization or PCR. It is assumed that the raffinose synthase gene originating from chromosome contains intron in its coding region. However, DNA divided into several parts by such intron is included in the DNA of the present invention provided that it codes for the raffinose synthase.

(3) Poly(A)$^+$RNA is fractionated into fractions in accordance with the molecular weight or the like. The fractions are subjected to an in vitro translation system based on the use of wheat germ or rabbit reticulocyte to determine a fraction containing mRNA coding for a polypeptide having the raffinose synthase activity. An objective cDNA fragment is prepared and obtained from the fraction.

(4) An anti-cucumber raffinose synthase antibody is prepared. Elements of a cDNA library are incorporated into a protein expression vector, and an appropriate host is infected therewith to express proteins encoded by cDNA's. An objective cDNA may be screened by using the foregoing antibody.

(5) Appropriate primers are synthesized on the basis of amino acid sequences of peptide fragments, and a sequence containing the terminal is amplified by means of the RACE method, followed by cloning thereof.

<3> Method for Producing Raffinose of the Present Invention

In the method for producing raffinose of the present invention, the raffinose synthase is allowed to act on sucrose and galactinol to produce raffinose. When the raffinose synthase is allowed to act on sucrose and galactinol, the galactose residue used for constructing galactinol is transferred to sucrose, and thus raffinose is produced. During this process, myo-inositol used for constructing galactinol is liberated.

The raffinose synthase, which is used to produce raffinose, may be an enzyme extracted from a plant body, or an enzyme produced by means of the genetic recombination technique based on the use of the DNA of the present invention.

In order to allow the raffinose synthase to act on sucrose and galactinol, the following procedure may be available. Namely, the raffinose synthase or cells having an ability to produce the raffinose synthase are immobilized to a carrier such as alginic acid gel and polyacrylamide gel to prepare immobilized enzyme or immobilized cells. The immobilized enzyme or the immobilized cells are charged to a column, and a solution containing sucrose and galactinol is allowed to pass through the column. As for the carrier and the method for immobilizing the raffinose synthase or the cells to the carrier, it is possible to adopt materials and methods which are used for ordinary bioreactors.

The raffinose synthesis reaction is performed, for example, by adding the raffinose synthase to a solution such as an aqueous solution or a buffer containing sucrose and galactinol. It is preferable that pH of the solution is adjusted to be within a range of about 6 to 8, especially at about pH 7. The reaction temperature is within a range of about 28 to 42° C., preferably 35 to 40° C., especially about 38° C. The raffinose synthase of the present invention is stable within a range of pH 5 to 8, especially in the vicinity of pH 6. The enzyme of the present invention is stable within a temperature range of not more than about 40° C.

The enzyme activity of the raffinose synthase of the present invention is inhibited by iodoacetamide, N-ethylmaleimide, $MnCl_2$, $ZnCl_2$, and $NiCl_2$. Therefore, it is desirable that these substances are not contained in the reaction solution.

Preferably, galactinol and sucrose are added to the reaction solution at a concentration of not less than 5 mM of galactinol and a concentration of not less than 1.5 mM of sucrose. The raffinose synthase may be added to the reaction solution in an amount depending on the amounts of the substrates.

Raffinose is separated from unreacted sucrose and galactinol and from myo-inositol produced by the enzyme reaction, contained in the reaction solution, in accordance with a method including, for example, gel filtration chromatography.

<4> Chimeric Gene and Transgenic Plant of the Present Invention

The chimeric gene of the present invention includes the raffinose synthase gene or a part thereof and the transcription regulatory region expressible in plant cells. The raffinose synthase gene is exemplified by the DNA coding for the raffinose synthase of the present invention described in the foregoing item <2>. When the chimeric gene of the present invention is used as an antisense gene, a non-coding region of the raffinose synthase gene or a part thereof can be used in some cases, besides the DNA coding for the raffinose synthase. The non-coding region includes, for example, sequences indicated by nucleotide numbers of 1 to 55 (5'-non-coding region) and nucleotide numbers of 2407 to 2517 (3'-non-coding region) in SEQ ID NO: 4 in Sequence Listing.

When the transcription regulatory region is linked to the DNA coding for the raffinose synthase in the chimeric gene of the present invention so that mRNA (sense RNA) homologous to the coding strand of the DNA is expressed, plant cells introduced with the chimeric gene express the raffinose synthase, and the content of the raffinose family oligosaccharides is increased. On the other hand, when the transcriptional regulatory region is linked to the DNA so that RNA (antisense RNA) having a sequence complementary to the coding strand of the DNA is expressed, and when the transcription regulatory region is linked to the DNA so that a partial fragment of the raffinose synthase gene, preferably sense RNA for a portion of not less than about 200 base pairs in the upstream coding region is expressed, then the expression of endogenous raffinose synthase is restrained in plant cells introduced with the chimeric gene, and the raffinose family oligosaccharides are decreased.

The content of the raffinose family oligosaccharides in a plant can be changed by transforming the plant with the chimeric gene of the present invention, and expressing the gene in cells of the plant.

Plants to which the present invention is applicable include, for example, oil crops such as soybean, rapeseed, cotton; sugar crops such as sugar beet and sugar cane; and model plants represented by *Arabidopsis thaliana*.

The transcription regulatory region expressible in plant cells includes, for example, promoters which make expression over a whole plant, such as CaMV 35S RNA promoter, CaMV 19S RNA promoter, and nopaline synthase promoter; promoters which make expression in green tissues, such as Rubisco small subunit promoter; and promoter regions which make site-specific expression at portions such as seed, including, for example, those for genes of napin and phaseolin as described above. The 3'-terminal of the chimeric gene may be connected with the terminator such as nopaline synthase terminator, and Rubisco small subunit 3'-end portion.

The plant may be transformed with the chimeric gene in accordance with usually used methods such as the Agrobacterium method, the particle gun method, the electroporation method, and the PEG method, depending on the host cell to be manipulated.

The transformation method for introducing the chimeric gene into the plant includes, for example, the Agrobacterium method, the particle gun method, the electroporation method, and the PEG method.

The Agrobacterium method is specifically exemplified by a method based on the use of a binary vector. Namely, a plant is infected with a vector comprising T-DNA originating from Ti plasmid, a replication origin which is functional in microorganisms such as *Escherichia coli*, and a marker gene for selecting plant cells or microbial cells harboring the vector. Seeds are collected from the plant, and they are allowed to grow. Plants introduced with the vector are selected by using an index of expression of the marker gene. Obtained plants are measured for the raffinose synthase activity, or strains exhibiting change in content of the raffinose family oligosaccharides are selected from the obtained plants. Thus it is possible to obtain an objective transformed plant.

A method for introducing the chimeric gene into soybean will be described below. In order to perform transformation for soybean, it is possible to use any one of the particle gun method (*Pro. Natl. Acad. Sci. USA*, 86, 145 (1989); *TIBTECH*, 8, 145 (1990); *Bio/Technology*, 6, 923 (1988); *Plant Physiol*, 87, 671 (1988); *Develop. Genetics*, 11, 289 (1990); and *Plant cell Tissue & Organ Culture*, 33, 227 (1993)), the Agrobacterium method (*Plant Physiol.*, 91, 1212 (1989); WO 94/02620; *Plant Mol. Biol.*, 9, 135 (1987); and *Bio/Technology*, 6, 915 (1933)), and the electroporation method (*Plant Physiol*, 99, 81 (1992); *Plant Physiol*, 84, 856 (1989); and *Plant Cell Reports*, 10, 97 (1991)).

In the particle gun method, it is preferable to use an embyogenic tissue or a hypocotyl of an immature seed about 30 to 40 days after dehiscence of anthesis. About 1 g of the embyogenic tissue is spread over a petri dish, into which, for example, gold particles or tungsten particles coated with the objective chimeric gene may be shot. The tissue is transferred after 1 to 2 hours to a liquid medium to perform cultivation. After 2 weeks, the tissue is transferred to a medium containing an antibiotic for transformant selection, followed by cultivation. After 6 weeks, a green adventitious embryo which is resistant to the antibiotic is obtained. The adventive embryo is further transferred to a fresh medium and cultured so that a plant body is reproduced. Alternatively, when the hypocotyl is used, the hypocotyl is excised under a sterilized condition, and it is treated in accordance with the particle gun method, followed by cultivation in MS medium (Murashige and Skoog, *Physiologia Plantrum*, 15, 473–497 (1962)) containing cytokinin at a high concentration. The hypocotyl is cultured in the darkness for 2 weeks, and then it is cultured at room temperature with light irradiation for 12 to 16 hours in MS medium having a lowered cytokinin content. During this process, it is preferable to add, to the medium, the antibiotic having been used as the selection marker. When a multiple bud body is formed from the transplanted tissue, it is transferred to a medium added with no hormone so that rooting is caused. An obtained seedling body is transferred to a greenhouse and cultivated.

In the case of the method based on the use of Agrobacterium, it is desirable to use Cotyldonary nod as a plant tissue. Commercially available LBA4404, C58, and Z707 can be used as Agrobacterium. However, it is desirable to use Z707. For example, a plasmid obtained by inserting the objective gene into pMON530 (produced by Monsanto Co.) can be used as the vector. The plasmid is introduced into *Agrobacterium tumefaciens* Z707 (Hepburn et al., *J. Gen. Microbiol.*, 131, 2961 (1985)) in accordance with, for example the Direct freeze thaw method (An et al., "Plant Mol. Biol. Mannual", A3: 1–19, 1988). The Agrobacterium transformed with the chimeric gene is cultivated overnight. Proliferated cells are collected by centrifugation at 5000 rpm for 5 minutes, and they are suspended in B5 suspension medium. Soybean seeds are sterilized, and they are cultivated for 3 days on B5 medium having a 1/10 concentration so that they germinate. Cotyledons are excised, and they are cultivated for 2 hours with the suspension of Agrobacterium. The cotyledons are transferred to B5 medium (containing Gamborg B5 salt (*Exp. Cell. Res.*, 50, 151 (1968)), Gamborg B5 vitamin, 3% sucrose, 5 $\mu$M benzylaminopurine, 10 $\mu$M IBA, and 100 $\mu$M acetosyringon), and they are cultivated for 3 days under a condition at 25° C. with light irradiation (60 $\mu$Em$^{-2}$S$^{-1}$) for 23 hours. Subsequently, in order to remove Agrobacterium, the cotyledons are cultivated in B5 medium (5 $\mu$M benzylaminopurine, 10 mg/L carbenicillin, 100 mg/L vancomycin, and 500 mg/L cefotaxime) at 25° C. for 4 days while exchanging the medium every day. After that, the cotyledons are cultivated in B5 medium (200 mg/L kanamycin). Multishoots are formed within 1 or 2 months. They are cultivated on B5 medium (0.58 mg/L gibberellin and 50 mg/L kanamycin) to elongate the shoots. Subsequently, the shoots are transferred to B5 medium (10 $\mu$M IBA) to cause rooting. Rooted seedlings are acclimatized, and they are cultivated in a greenhouse. Thus transformants can be obtained.

A transformant plant, in which the raffinose synthase gene is introduced, can be easily confirmed by extracting DNA from the transformant, and performing Southern hybridization by using the raffinose synthase gene as a probe.

BRIEF DESCRIPTION OF THE DRAWINGS

FIG. 7 shows relationships between synthetic primers and amino acid sequences of peptides. R represents A or G, Y represents C or T, M represents A or C, K represents G or T, D represents G, A, or T, H represents A, T, or C, B represents G, T, or C, N represents G, A, T, or C, and I represents inosine.

BEST MODE FOR CARRYING OUT THE INVENTION

Figure 1:
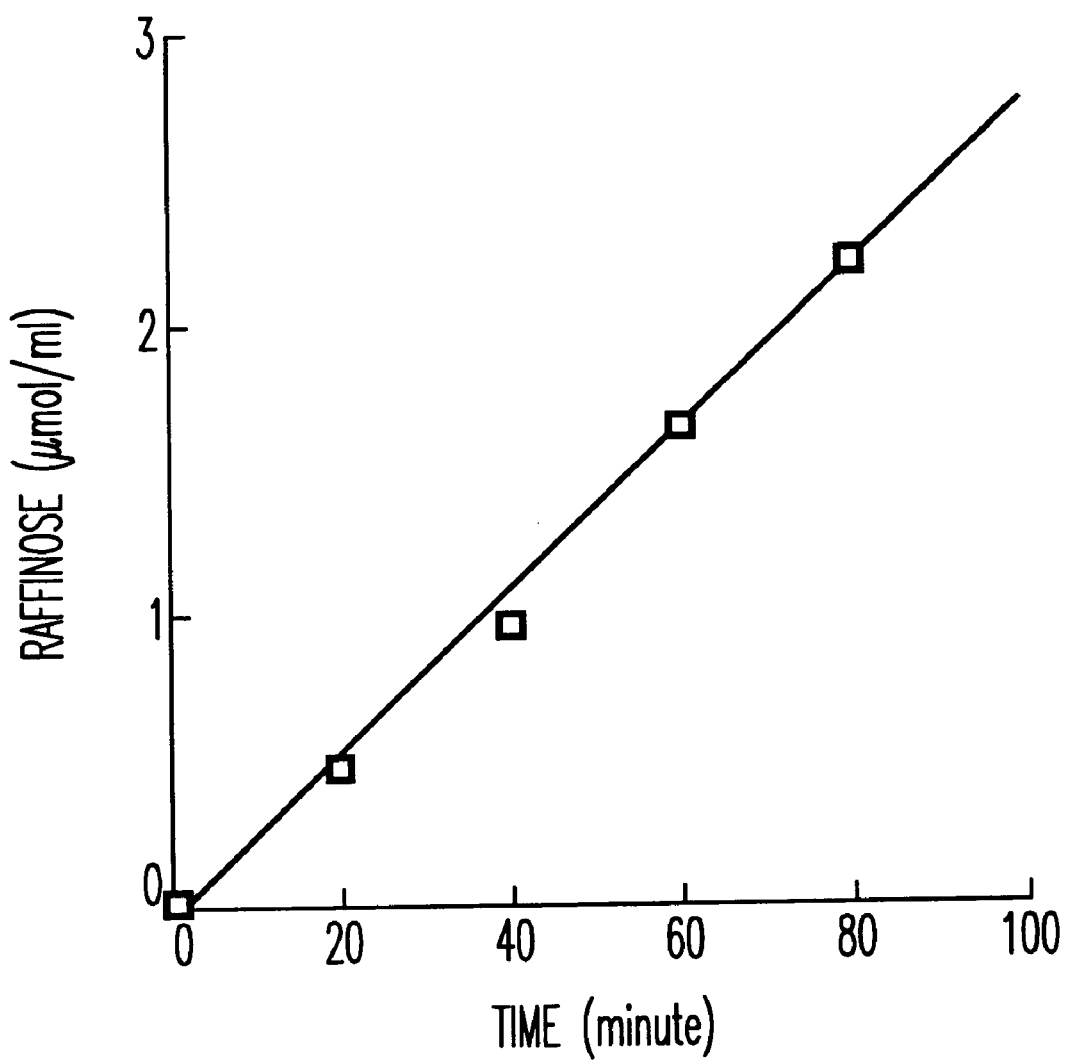
FIG. 1 shows a relationship between the reaction time and the amount of raffinose produced by the raffinose synthesis reaction.

The present invention will be more specifically explained below with reference to Examples.

At first, the method for measuring the raffinose synthase activity, used to confirm active fractions during respective purification steps and investigate characteristics of the enzyme in the following Examples, will be explained.

<Method for Measuring the Raffinose Synthase Activity>

The activity of the raffinose synthase was measured by quantitatively determining raffinose produced by the raffinose synthesis reaction by using HPLC (high-performance liquid chromatography). HPLC was performed by using Sugar Analysis System DX500 (CarboPac PA1 column, pulsed amperometry detector (produced by DIONEX)).

The raffinose synthesis reaction was performed by using a reaction solution prepared to have a composition having the following final concentrations. The reaction solution was added with 10 to 50 $\mu$l of a raffinose synthase solution to give a volume of 100 $\mu$l, followed by performing the reaction at 32° C. for 60 minutes.

[Composition of reaction solution (final concentration)]

2.5 mM sucrose 5 mM galactinol 5 mM DTT 20 mM Tris-HCl buffer (pH 7.0)

After performing the reaction as described above, the reaction solution was added with ethanol in a volume four times the volume of the reaction solution to stop the reaction by heating the solution at 95° C. for 30 seconds. The obtained solution was centrifuged to obtain a supernatant which was then dried up under a reduced pressure. After that, an obtained residue was dissolved in distilled water. Raffinose in the reaction product was quantitatively determined by using the sugar analysis system to estimate the raffinose synthase activity.

EXAMPLE 1

Purification of Raffinose Synthase from Cucumber

<1> Extraction of Raffinose Synthase from Cucumber

Vein tissues were collected from true leaves of cucumber (cv.: SUYOU) obtained 6 to 10 weeks after planting. The leaf vein tissues were frozen with liquid nitrogen, and they were stored at −80° C. The frozen leaf vein tissues were ground by a mortar with liquid nitrogen, to which Buffer 1 (40 mM Tris-HCl buffer (pH 7.0), 5 mM DTT, 1 mM PMSF (phenylmethanesulfonyl fluoride), 1% polyclarl AT (produced by Serva)) was added to extract proteins. An obtained extract solution was filtrated with a filter such as gauze or Miracloth (produced by Calbiochem-Novobiochem). An obtained filtrate was centrifuged at 4° C. at about 30,000×g for 60 minutes. A supernatant obtained by the centrifugation was used as a crude extract solution.

<2> Anion Exchange Chromatography (1)

The crude extract solution (about 560 ml) obtained as described above was applied to a column system comprising five connected columns for strongly basic anion exchange chromatography (HiTrap Q, produced by Pharmacia, 1.6 cm×2.5 cm) equilibrated with Buffer 2 (20 mM Tris-HCl buffer (pH 7.0), 5 mM DTT) to adsorb the raffinose synthase activity to the columns. Subsequently, the columns were washed with Buffer 3 (20 mM Tris-HCl buffer (pH 7.0), 0.2 M NaCl, 5 mM DTT) in a volume five times of the columns so that non-adsorbed proteins were washed out. After that, the raffinose synthase activity was eluted from the columns with 50 ml of Buffer 4 (20 mM Tris-HCl buffer (pH 7.0), 0.3 M NaCl, 5 mM DTT).

<3> Anion Exchange Chromatography (2)

The eluted solution (about 75 ml) was placed in a dialysis tube (Pormembranes MWC 0:10,000, produced by Spectra), and it was dialyzed against 10 L of Buffer 5 (20 mM Tris-HCl buffer (pH 7.0), 0.05 M NaCl, 5 mM DTT) at 4° C. overnight. The dialyzed sample was applied to a column for weakly basic anion exchange chromatography (DEAE-TOYOPEARL, produced by Toyo Soda, 2.2×20 cm) equilibrated with Buffer 5 to adsorb the raffinose synthase activity to the column. Subsequently, the column was washed with Buffer 5 in a volume five times the volume of the column to wash out non-adsorbed proteins. After that, a linear concentration gradient of 0.05 M to 0.35 M NaCl in a volume twenty times the volume of the column was applied to elute the enzyme activity so that fractionation was performed.

<4> Gel Filtration Chromatography

The eluted solution obtained as described above (about 160 ml) was concentrated into 6.5 ml by using a concentrator (Centriprep 10, produced by Amicon). Aliquots (each 3 ml) of the concentrated solution were applied to a column for gel filtration chromatography (Superdex 200 pg, produced by Pharmacia, 2.6 cm×60 cm). Equilibration for the column and elution from the column were performed by using Buffer 6 (20 mM Tris-HCl buffer (pH 7.0), 0.1 M NaCl, 5 mM DTT, 0.02% Tween 20). Fractions having the raffinose synthase activity were collected from fractionated fractions.

<5> Hydroxyapatite Chromatography

A collected fraction (about 25 ml) having the raffinose synthase activity fractionated by the gel filtration was concentrated by using Centriprep 10, and the buffer was exchanged with Buffer 7 (0.01 M sodium phosphate buffer (pH 7.0), 5 mM DTT, 0.02% Tween 20). An obtained concentrate solution (about 1.2 ml) was applied to a hydroxyapatite column (Bio-Scale CHT-1, produced by Bio Rad, 0.7×5.2) previously equilibrated with the same buffer to adsorb the raffinose synthase activity. The column was washed with the same buffer in a volume (10 ml) five times the volume of the column. After that, a linear concentration gradient of 0.01 M to 0.3 M phosphate in a volume twenty times the volume of the column was applied to elute the enzyme activity so that fractionation was performed.

<6> Hydroxyapatite Rechromatography

An active fraction obtained in accordance with the hydroxyapatite chromatography as described above was subjected to rechromatography in the same manner as described above to obtain a purified raffinose synthase fraction (about 2 ml).

The amount of protein contained in the active fraction was about 200 μg. The total activity was 5700 nmol/hour, and the specific activity per protein was 28 μmol/hour/mg. The active fraction contained only a protein which exhibited a single band corresponding to a molecular weight of 90 kDa to 100 kDa on electrophoresis as described later on. The specific activity of the obtained purified enzyme sample was about 2000 times that of the crude extract solution. The recovery was 12% with respect to the amount of the enzyme obtained after the strongly basic anion exchange chromatography based on the use of HiTrap Q. Results of the purification are summarized in Table 1.

TABLE 1

|  | Total protein mg | Total activity nmol/h | Specific activity nmol/h/mg | Yield % |
| --- | --- | --- | --- | --- |
| Crude extract | 1915 | 20700 | 11 | — |
| HiTrap Q | 1092 | 48800 | 45 | 100 |
| DEAE-TOYOPEARL | 540 | 33000 | 61 | 68 |
| Superdex 200 pg | 1.79 | 26500 | 14800 | 54 |
| Apatite (1)* | 0.51 | 12600 | 24700 | 26 |
| Apatite (2)* | 0.20 | 5700 | 28500 | 12 |

Apatite (1)*: Hydroxyapatite chromatography (1)
Apatite (2)*: Hydroxyapatite chromatography (2)

EXAMPLE 2

Investigation on Characteristics of Raffinose Synthase

Characteristics of the purified raffinose synthase obtained in Example 1 were investigated.

<1> Molecular Weight Measurement (1) Gel Filtration Chromatography

An aliquot (10 μl) of the purified raffinose synthase was dispensed. This sample and a molecular weight marker (Molecular Weight Marker Kit for Gel Filtration, produced by Pharmacia) were applied to a gel filtration chromatography column (Superdex 200 pg, produced by Pharmacia). Equilibration of the column and elution from the column were performed by using Buffer 6 (20 mM Tris-HCl buffer (pH 7.0), 0.1 M NaCl, 5 mM DTT, 0.02% Tween 20). As a result, the molecular weight of the raffinose synthase was estimated to be about 75 kDa to 95 kDa.

(2) Polyacrylamide Gel Electrophoresis (Native PAGE)

An aliquot (10 μl) of the purified raffinose synthase was dispensed, to which the same volume of a sample buffer (0.0625 M Tris-HCl (pH 6.8), 15% glycerol, 0.001% BPB) was added to prepare an electrophoresis sample. The sample (10 μl) was applied to 10% polyacrylamide gel (produced by Daiichi Chemical, Multigel 10), and electrophoresed at 40 mA for about 60 minutes with 0.025 M Tris–0.192 M glycine buffer (pH 8.4). After the electrophoresis, the gel was stained with Silver Stain Kit (produced by nacalai tesque). As a result, the molecular weight was estimated to be about 90 kDa to 100 kDa.

(3) SDS-polyacrylamide Gel Electrophoresis (SDS-PAGE)

Figure 2:
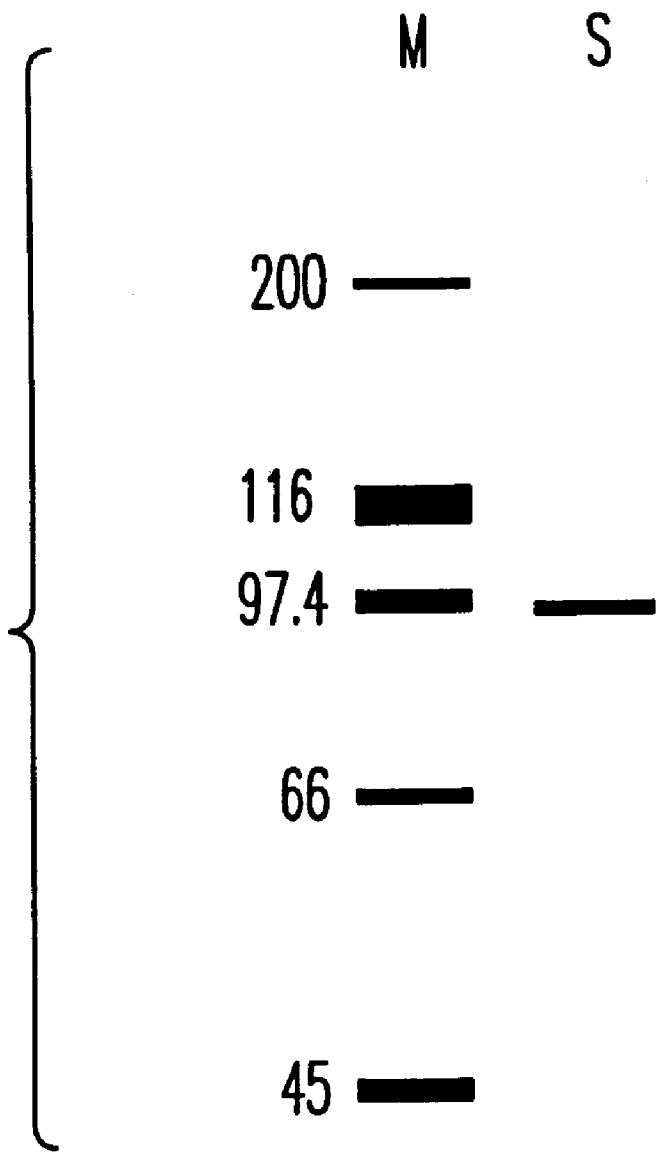
FIG. 2 shows a photograph illustrating a result of SDS-polyacrylamide gel electrophoresis for the raffinose synthase. M indicates molecular weight markers, and S indicates a sample containing the raffinose synthase. Numerals indicate molecular weights (kDa).

An aliquot (10 μl) of the purified raffinose synthase was dispensed, to which the same volume of a sample buffer (0.0625 M Tris-HCl (pH 6.8), 2% SDS, 10% glycerol, 5% mercaptoethanol, 0.001% BPB) was added, followed by heating in a boiling water bath for 1 minute to prepare an electrophoresis sample. The sample (10 μl) was applied to 10 to 20% gradient polyacrylamide gel (produced by Daiichi Chemical), and electrophoresed at 40 mA for about 70 minutes with 0.025 M Tris–0.192 M glycine buffer (pH 8.4) containing 0.1% SDS. After the electrophoresis, the gel was stained with Silver Stain Kit (produced by nacalai tesque). A result is shown in FIG. 2. As a result, the molecular weight was estimated to be about 90 kDa to 100 kDa.

<2> Optimum Reaction Temperature

Figure 3:
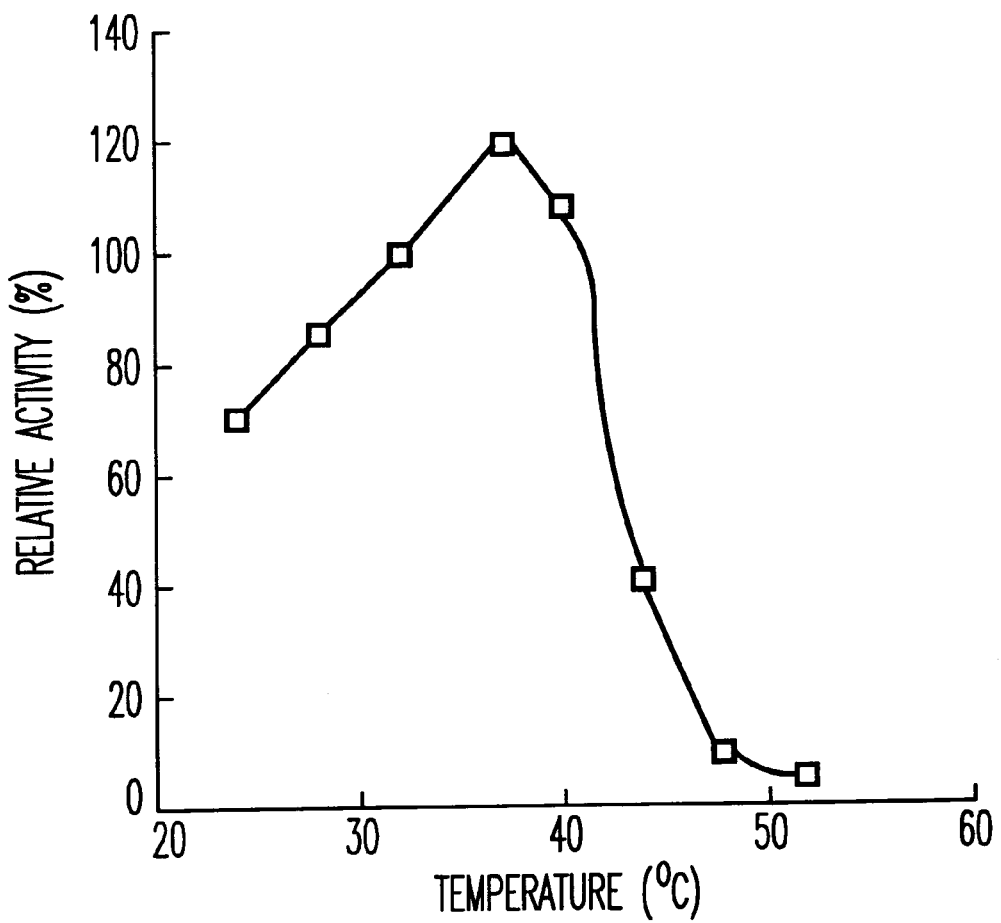
FIG. 3 shows an influence of the reaction temperature on the raffinose synthase activity.

The raffinose synthase activity was measured under various temperature conditions (28° C., 32° C., 36° C., 40° C., 44° C., 48° C., and 52° C.) in accordance with the method for measuring the raffinose synthase activity described above. The enzyme solution was added to the respective reaction solutions in an amount of 2 µl. FIG. 3 shows relative activities at the respective temperatures assuming that the enzyme activity at 32° C. was 100. As a result, the raffinose synthase exhibited the activity in a range of about 25 to 42° C., and the optimum reaction temperature was about 35 to 40° C.

<3> Optimum Reaction pH

Figure 4:
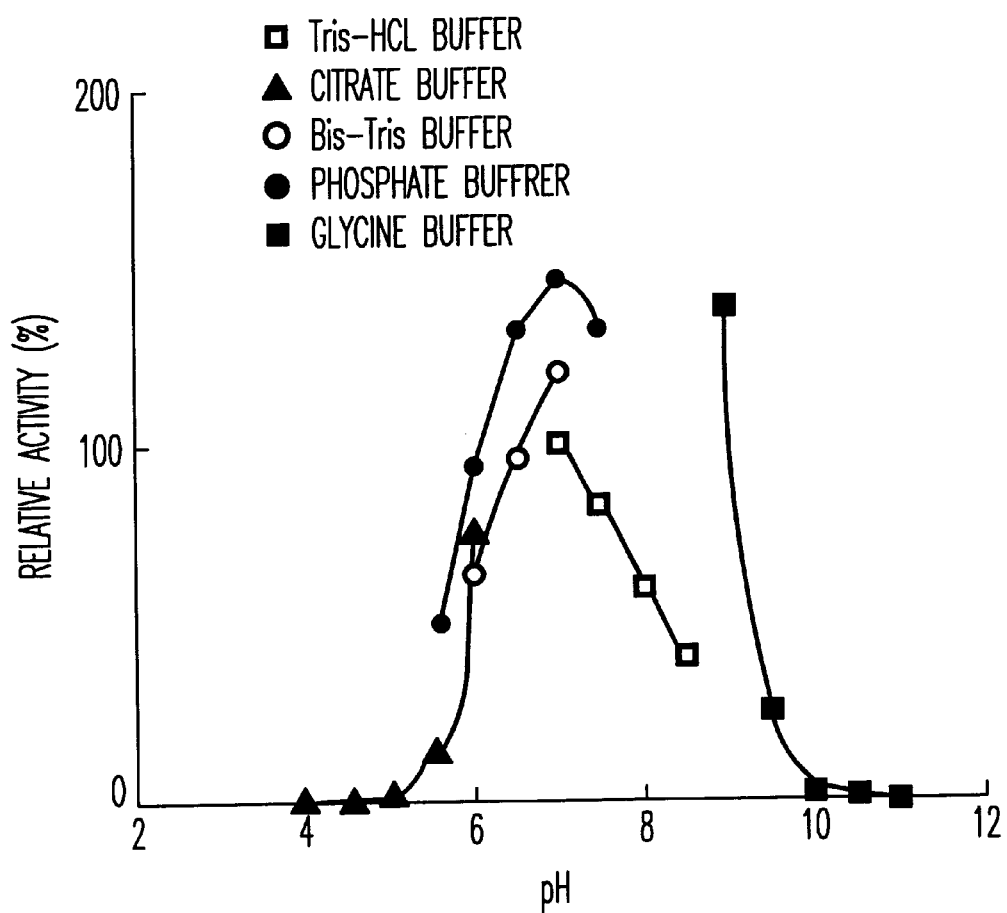
FIG. 4 shows an influence of the reaction pH on the raffinose synthase activity.

The raffinose synthase activity was measured under various pH conditions (pH 4 to 11) in accordance with the method for measuring the raffinose synthase activity described above. The respective reactions were performed by using 50 mM citrate buffer (pH 4 to 6), 50 mM potassium phosphate buffer (pH 5.5 to 7.5), 50 mM Bis-Tris buffer (pH 6 to 7), 20 mM Tris-HCl buffer (pH 7 to 8.5), and 50 mM glycine-NaOH buffer (pH 9 to 11). The enzyme solution was added to the respective reaction solutions in an amount of 2 µl. A result is shown in FIG. 4.

As a result, the raffinose synthase exhibited the activity in a range of pH 5 to 10, and the optimum reaction pH was about 6 to 8, provided that the activity varied depending on the type of the buffer used for the measurement.

<4> Investigation on Inhibitors and Metal Ions

Various enzyme inhibitors or metal ions were added to the reaction solution of the purified raffinose synthase to give a final concentration of 1 mM respectively, and the raffinose synthase activity was measured in the same manner as described above. Table 2 shows remaining activities with respect to the enzyme activity obtained when neither inhibitor nor metal ion was added. Iodoacetamide and N-ethylmaleimide clearly inhibited the enzyme activity. The inhibiting effect was scarcely observed for $CaCl_2$, $CuCl_2$, and $MgCl_2$. However, $MnCl_2$, $ZnCl_2$, and $NiCl_2$ exhibited the inhibiting effect.

TABLE 2

| Inhibitor or metal ion | Remaining activity (%) |
|---|---|
| No addition | 100 |
| Iodoacetoamide | 0 |
| N-ethylmaleimide | 40 |
| $CaCl_2$ | 115 |
| $CuCl_2$ | 101 |
| $MgCl_2$ | 96 |
| $MnCl_2$ | 32 |
| $ZnCl_2$ | 42 |
| $NiCl_2$ | 68 |

<5> Inhibition by Myo-inositol

Figure 5:
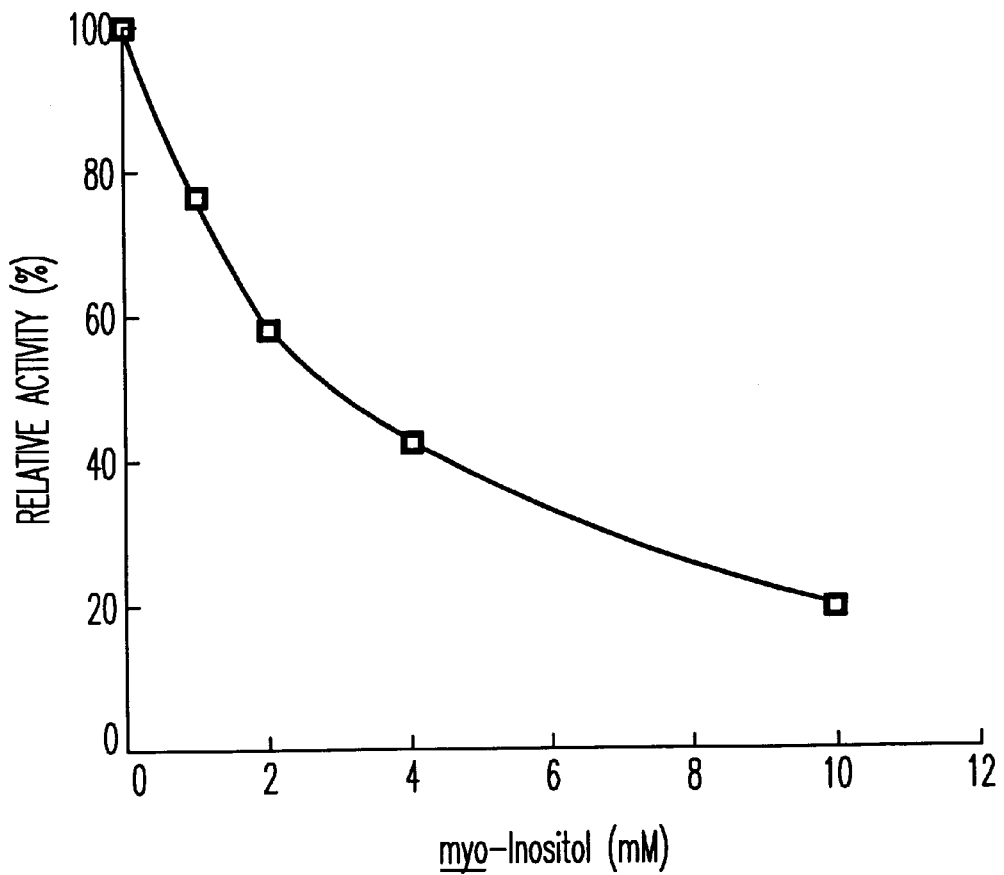
FIG. 5 shows an influence of myo-inositol on the raffinose synthase activity.

Investigation was made for inhibition by myo-inositol as the reaction product of the raffinose synthesis reaction. The reaction solution was added with myo-inositol at various concentrations, and the raffinose synthase activity was measured. A result is shown in FIG. 5. The enzyme activity was inhibited as the concentration of added myo-inositol was increased.

<6> Stable pH

Figure 6:
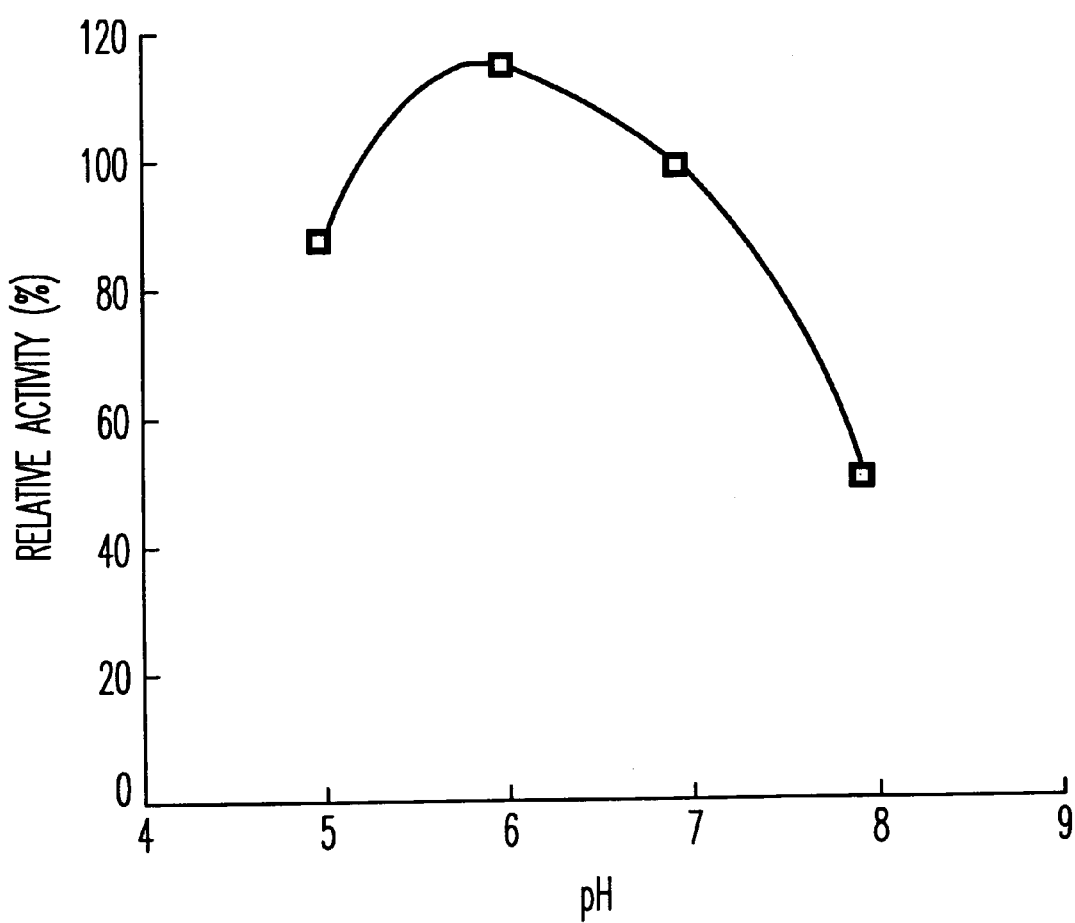
FIG. 6 shows a stable pH range of the raffinose synthase.

The raffinose synthase fraction obtained by the anion exchange chromatography (2) described above was incubated for 4 hours at 4° C. in 50 mM Bis-Tris-HCl buffer (pH 5 to 8.0, containing 0.5 mM DTT) or 20 mM Tris-HCl buffer (pH 7 to 8.0, containing 0.5 mM DTT), and then the raffinose synthase activity was measured. FIG. 6 shows the enzyme activity versus pH of the buffer used for the incubation. The raffinose synthase activity was confirmed after the incubation under any of the incubation conditions. Especially, the enzyme was stable in a range of pH 5 to 7.5.

<7> Stable Temperature

The raffinose synthase fraction obtained by the anion exchange chromatography (2) described above was incubated in 20 mM Tris-HCl buffer (pH 7, containing 0.5 mM DTT) for 60 minutes at 28° C., 32° C., 37° C., or 40° C., and then the raffinose synthase activity was measured. As a result, the enzyme of the present invention was stable, exhibiting, in the range of 28° C. to 40° C., activities of 80% to 100% of that obtained by a control for which the incubation treatment was not performed for comparison.

<8> Analysis of Amino Acid Sequence

The cysteine residue of the purified raffinose synthase was subjected to reducing pyridylethylation, and the reaction mixture was desalted. An obtained sample was digested at 37° C. for 12 hours with lysylendopeptidase (Achromobacter protease 1, produced by Wako Pure Chemical Industries) to form peptide fragments. An obtained peptide mixture was applied to reverse phase HPLC (column: Waters µBondasphere (φ2.1×150 mm, $C_{18}$, 300 Å, produced by Waters (Millipore))) to separate and obtain the respective peptide fragments. 0.1% TFA (trifluoroacetic acid) was used as a solvent, and elution was performed with a concentration gradient of acetonitrile. Amino acid sequences of three fragments selected from the obtained peptide fragments were determined by using a protein sequencer. The determined amino acid sequences of the respective peptides are shown in SEQ ID NOs: 1 to 3 in Sequence Listing. These peptides will be thereafter referred to as Peptides 1, 2, and 3 respectively in this order.

EXAMPLE 3

Preparation of DNA Coding for Raffinose Synthase

<1> Isolation of Partial Fragment of cDNA of Raffinose Synthase by Means of PCR Method Major veins of cucumber (22 g) were ground by a mortar with liquid nitrogen. The ground material was added to a mixture of an extraction buffer (100 mM lithium chloride, 100 mM Tris-HCl (pH 8.0), 10 mM EDTA, and 1% SDS) and an equal amount of phenol previously heated to 80° C., followed by agitation. After that, a mixture of phenol and an equal amount of chloroform: isoamyl alcohol (24:1) was added thereto, followed by agitation again. An obtained mixture solution was centrifuged at 4° C. at 9250×g for 15 minutes to collect a supernatant. The supernatant was repeatedly subjected to the treatment with phenol and the treatment with chloroform: isoamyl alcohol to obtain a supernatant after centrifugation. The supernatant was added with an equal amount of 4 M lithium chloride, followed by being stationarily left to stand at −70° C. for 1 hour.

After thawing at room temperature, the sample was treated and centrifuged at 4° C. at 9250×g for 30 minutes to obtain a precipitate. The precipitate was washed with 2 M lithium chloride once and with 80% ethanol once. After drying, the precipitate was dissolved in 2 ml of a diethylpyrocarbonate-treated solution to give a sample of purified total RNA. The obtained total RNA was 2.38 mg.

The all amount of the total RNA was applied to poly(A)$^+$ RNA purification kit (produced by STRATAGENE CLONING SYSTEMS) based on the use of an oligo(dT) cellulose column so that poly(A)$^+$RNA molecules were purified to obtain 42.5 µg of poly(A)$^+$RNA.

Single strand cDNA's were synthesized from poly(A)$^+$ RNA obtained as described above, by using reverse transcriptase Super Script II (produced by GIBCO BRL). In order to isolate raffinose synthase cDNA from an obtained cDNA mixture, amplification was performed in accordance with the PCR method. In order to be used as primers in PCR, single strand oligonucleotides (SEQ ID NOs: 6 to 22) shown in FIG. 7 were synthesized on the basis of the amino acid sequences of the peptide fragments of the raffinose synthase originating from cucumber, determined in Example 2. In the sequences of the respective primers, R represents A or G, Y represents C or T, M represents A or C, K represents G or T, D represents G, A, or T, H represents A, T, or C, B represents G, T, or C, N represents G, A, T, or C, and I represents inosine (base: hypoxanthine) respectively.

A DNA fragment of about 540 base pairs was amplified when the primers were combined and used such that the 5'-side primer was A (A1 (SEQ ID NO: 6), A2 (SEQ ID NO: 7), A3 (SEQ ID NO: 8), A4 (SEQ ID NO: 9)) and the 3'-side primer was D' (D'1 (SEQ ID NO: 21), D'2 (SEQ ID NO: 22)), or the 5'-side primer was C2 (SEQ ID NO: 14) and the 3'-side primer was B'1 (SEQ ID NO: 18) or B'2 (SEQ ID NO: 19). The fragment was cloned into a plasmid pCRII by using TA cloning kit (produced by INVITROGEN BV) to analyze its nucleotide sequence. As a result, a nucleotide sequence coding for the amino acid sequences of Peptides 1, 2 was found inwardly between the primer sequences at both terminals. Accordingly, it was found that the amplified fragment is a DNA fragment originating from the raffinose synthase gene.

In order to specify the position of the cloned PCR-amplified DNA fragment on the raffinose synthase gene, 3'-RACE was performed by using RACE kit (3' Ampifinder RACE Kit, produced by CLONTACH).

PCR was performed by using the cDNA mixture as a template, C (C1 (SEQ ID NO: 13), C2 (SEQ ID NO: 14)) as a 5'-side primer, and a primer having oligo(dT) and an anchor sequence as a 3'-side primer. Further, PCR was performed by using an amplified fragment thus obtained as a template, D (D1 (SEQ ID NO: 15), D2 (SEQ ID NO: 16)) located inwardly from C as a 5'-side primer, and an oligo (dT)-anchor primer as a 3'-side primer. As a result, a DNA fragment of about 2400 base pairs was amplified only when PCR was performed by using, as the template, DNA amplified with C1 (SEQ ID NO: 13) or C2 (SEQ ID NO: 14) and the oligo(dT)-anchor primer, and using D2 (SEQ ID NO: 16) and the oligo(dT)-anchor primer. Further, PCR was performed by using C (C1 (SEQ ID NO: 13), C2 (SEQ ID NO: 14)) as the 5'-side primer and the oligo(dT)-anchor primer as the 3'-side primer, and then PCR was performed by using the amplified fragment thus obtained as a template, E (SEQ ID NO: 17) as a 5'-side primer, and the oligo(dT)-anchor primer as a 3'-side primer. As a result, a DNA fragment of about 300 base pairs was amplified in any case.

Similarly, PCR was performed by using A (A1 (SEQ ID NO: 6), A2 (SEQ ID NO: 7), A3 (SEQ ID NO: 8), or A4 (SEQ ID NO: 9)) as a 5'-side primer, and the primer having oligo(dT) and the anchor sequence as a 3'-side primer. Further, PCR was performed by using an amplified fragment thus obtained as a template, and using B (B1 (SEQ ID NO: 10), B2 (SEQ ID NO: 11), or B3 (SEQ ID NO: 12)) located inwardly from A as a 5'-side primer, and the same oligo (dT)-anchor primer as a 3'-side primer. As a result, a DNA fragment of about 2000 base pairs was obtained when the B2 primer was used even when any of the A primers was used. Thus the DNA fragment amplified by using the A2 and B2 primers was cloned. As a result of nucleotide sequence analysis, the DNA fragment included the nucleotide sequence coding for the amino acid sequence of Peptide fragment 1 used to prepare the 5'-side primer. The DNA fragment also included, on the 3'-side, the poly(A) sequence and the nucleotide sequence corresponding to Peptide fragment 3 at a position located upstream therefrom.

In view of the result of PCR described above, it was found that Peptide fragments of the raffinose synthase are arranged from the N-terminal side in an order of 2, 1, 3, and the DNA fragment of about 540 base pairs previously obtained by PCR was a portion located near to the 5'-terminal on the raffinose synthase gene. In order to screen a cDNA clone containing the entire length of the raffinose synthase gene, it is desirable that DNA to be used as a probe can detect a portion near to the 5'-terminal side. Accordingly, the obtained DNA fragment was used as a probe to perform screening for a cDNA library.

<2> Cloning of Entire Length of Coding Region of Raffinose Synthase cDNA

At first, a cDNA library was prepared as follows. Double strand cDNA's were synthesized from poly(A)$^+$RNA (3.8 μg) obtained in the foregoing item <1> by using Time Saver cDNA synthesis kit (produced by Pharmacia Biotech). Obtained cDNA's were incorporated into EcoRI restriction enzyme cleavage site of λ phage vector, λMOSSlox (produced by Amersham) respectively, which were then incorporated into the phage protein by using GigapackII Gold packaging kit (produced by STRATAGENE CLONING SYSTEMS). Thus the cucumber cDNA library was prepared. This library had a titer of $1.46 \times 10^7$ pfu/μg vector.

Host cells of *Escherichia coli* ER1647 were infected with the phages contained in the cucumber cDNA library in an amount corresponding to $1.4 \times 10^5$ pfu, and then the cells were spread over 14 agar plates each having a diameter of 90 mm to give $1.0 \times 10^4$ pfu per one plate. The cells were cultivated at 37° C. for about 6.5 hours. After that, phage plaques formed on the plates were transferred to nylon membranes (Hybond-N+, produced by Amersham).

Next, the nylon membranes were treated with alkali to denature transferred DNA, followed by neutralization and washing. After that, the nylon membranes were treated at 80° C. for 2 hours to fix DNA on the membranes.

Positive clones were screened on the obtained nylon membrane by using the DNA fragment of about 540 base pairs obtained in the foregoing item <1> as a probe. The DNA fragment of about 540 base pairs was digested with restriction enzyme EcoRI, followed by electrophoresis to excise and purify only the insert of about 540 base pairs. The insert was labeled with fluorescein by using DNA labeling and detection system (Gene Images labeling and detection system, produced by Amersham) to be used as the probe. The nylon membranes were subjected to prehybridization at 60° C. for 30 minutes, and then the labeled probe was added to perform hybridization at 60° C. for 16 hours. An antibody (alkaline phosphatase-labeled anti-fluorescein antibody) for detecting the labeled DNA was used after being diluted 50000 times. In this screening process, candidate strains for positive clones were obtained. The obtained candidate strains were further subjected to repeated screening twice in the same manner as described above to obtain a purified positive clone.

*Escherichia coli* BM25.8 was infected with the positive clone, and it was cultivated on a selection medium containing carbenicillin. A plasmid vector λMOSSlox-CRS containing cDNA was excised therefrom. The inserted cDNA of the plasmid had a length of about 2.5 kb. *Escherichia coli* JM109 was transformed with the plasmid. Plasmid DNA was prepared from a transformant, which was used as a sample for analyzing the nucleotide sequence.

The nucleotide sequence of the inserted cDNA was analyzed by using Taq DyeDeoxy Terminator Cycle Sequencing Kit (produced by Perkin-Elmer) in accordance with the conventionally known method.

As a result, a nucleotide sequence comprising 2352 base pairs as shown in SEQ ID NO: 4 in Sequence Listing was revealed. The sequence included a portion coincident with the nucleotide sequence of the DNA probe used by the present inventors. An amino acid sequence translated from the nucleotide sequence is shown in SEQ ID NOs: 4 and 5. The amino acid sequence included portions coincident with Peptide 1 (amino acid numbers of 215 to 244 in SEQ ID NO: 5), Peptide 2 (amino acid numbers of 61 to 79 in SEQ ID NO: 5), and Peptide 3 (amino acid numbers of 756 to 769 in SEQ ID NO: 5) of the raffinose synthase originating from cucumber obtained by the present inventors. Thus it was confirmed that the amino acid sequence codes for the raffinose synthase.

The transformant, designated as AJ13263, of *Escherichia coli* JM109, which harbors the plasmid pMossloxCRS containing DNA coding for the raffinose synthase obtained as described above, has been internationally deposited on the basis of the Budapest Treaty since Nov. 19, 1996 in National Institute of Bioscience and Human Technology of Agency of Industrial Science and Technology of Ministry of International Trade and Industry (postal code: 305, 1-3 Higashi-Icchome, Tsukuba-shi, Ibaraki-ken, Japan), and awarded a deposition number of FERM BP-5748.

EXAMPLE 4

Chimeric Gene and Transformed Plant Containing DNA Coding for Raffinose Synthase <1> Construction of Plasmid Containing Chimeric Gene The DNA fragment coding for the raffinose synthase was introduced into *Arabidopsis thaliana* by using LBA4404 as Agrobacterium and pBI121 (produced by CLONTECH) as a binary vector. pBI121 is a plasmid originating from pBIN19, which comprises nopaline synthase gene promoter connected to neomycin phosphotransferase structural gene (NPTII), nopaline synthase gene terminator (Nos-ter), CaMV 35S promoter, GUS (β-glucuronidase) gene, and Nos-ter, and which has sequences for enabling transposition to plant, on both sides thereof. A SmaI site is located downstream from CaMV 35S promoter. An insert inserted into this site is expressed under the regulation of the promoter.

A fragment of the raffinose synthase gene obtained in Example 3 was inserted into the binary vector pBI121. The raffinose synthase gene was digested with DraI to prepare, by means of agarose gel electrophoresis, a DNA fragment containing 30th to 1342th nucleotides in SEQ ID NO: 4 in Sequence Listing. This fragment was ligated into the SmaI site of pBI121. *Escherichia coli* HB101 was transformed with the ligation reaction solution to obtain transformant strains from which recombinant plasmids were prepared. Two recombinant plasmids, in which the raffinose synthase DNA fragment was reversely connected to CaMV 35S promoter (antisense), and the raffinose synthase DNA fragment was connected to CaMV 35S promoter in the positive direction (sense), were selected from the obtained recombinant plasmids. The two recombinant plasmids were designated as pBIRS1 and pBIRS9 respectively.

Each of the plasmids obtained as described above was introduced into Agrobacterium LBA4404 by means of triparental mating.

*Arabidopsis thaliana* was transformed as follows. Seeds of *Arabidopsis thaliana* was subjected to a treatment for water absorption. After that, they were sterilized by treating them with 80% ethanol containing 1% Tween 20 for 5 minutes, and treating them with 10% sodium hypochlorite solution also containing 1% Tween 20 for 10 minutes, followed by washing five times with sterilized water. The seeds were suspended in 1% low melting point agarose, and they were spread over an MS medium (MS basic medium (Murashige and Skoog, *Physiologia Plantrum*, 15, 473–497 (1962)), B5 vitamin, 10 g/L sucrose, 0.5 g/L MES, pH 5.8). The seeds were cultivated at 22° C. for 1 week in a culture room to give a cycle comprising light irradiation for 16 hours and darkness for 8 hours. Plants with unfolded seed leaves were subjected to setting with rock wool. Cultivation was continued under the same condition. After about 3 weeks, decapitation was performed when the plants caused bolting to have heights of stems of several cm's. The plants were allowed to grow until a state in which first flowers bloom on elongated branches 1 week after the decapitation.

Agrobacterium harboring the introduced recombinant plasmid containing the raffinose synthase gene was precultivated in 2 ml of LB medium. An obtained culture was inoculated into LB medium containing 50 mg/L kanamycin and 25 mg/L streptomycin, followed by cultivation at 28° C. for about 1 day. Bacterial cells were collected at room temperature, and they were suspended in a suspension medium for infiltration (1/2 MS salt, 1/2 Gamborg B5 vitamin, 5% sucrose, 0.5 g/L MES, pH 5.7 (KOH), to which, immediately before the use, benzylaminopurine was added to give a final concentration of 0.044 μM, or Silwet L77 was added in an amount of 200 μl per 1 L (final concentration: 0.02%)) so that $OD_{600}$ of an obtained bacterial suspension was 0.8.

Flowers in bloom and fructification were removed from the plants to be subjected to infiltration. The rock wool was inverted upside down, and flowers which were not in fructification were immersed in the suspension of Agrobacterium, followed by being placed in a desiccator so that the pressure was reduced to be 40 mmHG for 15 minutes. Seeds were harvested after 2 to 4 weeks. The harvested seeds were stored in a desiccator.

Next, transformants were selected on a selection medium. The seeds were sterilized in the same manner as described above, and they were cultivated on a selection medium (MS salt, Gamborg B5 vitamin, 1% sucrose, 0.5 g/L MES, pH 5.8, 0.8% agar, to which antibiotics for selection, i.e., carbenicillin (final concentration: 100 mg/L) and kanamycin (final concentration: 50 mg/L) were added after autoclaving)) at 22° C. to select resistant plants. The resistant plants were transferred to a fresh medium, and they were allowed to grow until true leaves unfolded. Seeds were harvested from the obtained plants. Selection was repeated in the same manner as described above, and thus T3 seeds were obtained. The T3 seeds were measured for the raffinose content in accordance with the method described above. Results are shown in Table 4.

TABLE 4

| Plant | Raffinose content (mg/g) |
| --- | --- |
| Wild type | 0.2 |
| Transformant (pBIRS1) | 0.0 |
| Transformant (pBIRS9) | 0.0 |

INDUSTRIAL APPLICABILITY

The present invention provides the purified raffinose synthase, the raffinose synthase gene, the chimeric gene comprising the raffinose synthase gene and the regulatory region expressible in plants, and the plant introduced with the chimeric gene.

Raffinose can be efficiently synthesized from sucrose and galactinol by using the raffinose synthase of the present invention. The content of the raffinose family oligosaccharides in plants can be changed by utilizing the raffinose synthase gene or the chimeric gene of the present invention.

What is claimed is:

1. An isolated DNA coding for a protein which has the amino acid sequence of SEQ ID NO: 5.

2. An isolated DNA selected from the group consisting of:
   (a) an isolated DNA comprising at least nucleotide residues 57 to 2408 of SEQ ID NO: 4; and
   (b) an isolated DNA which originates from an organism having an ability to produce raffinose from sucrose and galactinol, which is hybridizable under a stringent condition with the nucleotide sequence comprising at least nucleotide residues 57 to 2408 of the nucleotide sequence of SEQ ID NO: 4, and which codes for a protein that produces raffinose from sucrose and galactinol.

3. The DNA according to claim 2, wherein the organism is a plant.

4. The DNA according to claim 2, which is (a).

5. The DNA according to claim 2, which is (b).

6. A chimeric gene comprising a raffinose synthase gene, and a transcription regulatory region expressible in plant cells, wherein the transcription regulatory region is linked to the raffinose synthase gene so that a mRNA homologous to the coding strand of the raffinose synthase gene is expressed.

7. The chimeric gene according to claim 6, wherein the raffinose synthase gene comprises a DNA coding for a protein which has the amino acid sequence of SEQ ID NO: 5.

8. The chimeric gene according to claim 6, wherein the raffinose synthase gene comprises a DNA selected from the group consisting of:
   (a) a DNA comprising at least nucleotide residues 57 to 2408 of SEQ ID NO: 4; and
   (b) a DNA which originates from an organism having an ability to produce raffinose from sucrose and galactinol, which is hybridizable under a stringent condition with the nucleotide sequence comprising at least nucleotide residues 57 to 2408 of the nucleotide sequence of SEQ ID NO: 4, and which codes for a protein that produces raffinose from sucrose and galactinol.

9. The chimeric gene according to claim 8, wherein the organism is a plant.

10. The chimeric gene according to claim 8, wherein the raffinose synthase gene comprises (a).

11. The chimeric gene according to claim 8, wherein the raffinose synthase gene comprises (b).

12. A chimeric gene comprising a raffinose synthase gene or a part thereof, and a transcription regulatory region expressible in plant cells, wherein the transcription regulatory region is linked to the raffinose synthase gene or the part thereof so that an RNA having a sequence complementary to the coding strand of the raffinose synthase gene or the part thereof is expressed.

13. The chimeric gene according to claim 12, wherein the raffinose synthase gene comprises a DNA coding for a protein which has the amino acid sequence of SEQ ID NO: 5.

14. The chimeric gene according to claim 12, wherein the raffinose synthase gene comprises a DNA selected from the group consisting of:
   (a) a DNA comprising at least nucleotide residues 57 to 2408 of SEQ ID NO: 4; and
   (b) a DNA which originates from an organism having an ability to produce raffinose from sucrose and galactinol, which is hybridizable under a stringent condition with the nucleotide sequence comprising at least nucleotide residues 57 to 2408 of the nucleotide sequence of SEQ ID NO: 4, and which codes for a protein that produces raffinose from sucrose and galactinol.

15. The chimeric gene according to claim 14, wherein the organism is a plant.

16. The chimeric gene according to claim 14, which is (a).

17. The chimeric gene according to claim 14, which is (b).

18. A plant which is transformed with the chimeric gene as defined in claim 6.

19. A plant which is transformed with the chimeric gene as defined in claim 7.

20. A plant which is transformed with the chimeric gene as defined in claim 8.

21. A plant which is transformed with the chimeric gene as defined in claim 9.

22. A plant which is transformed with the chimeric gene as defined in claim 10.

23. A plant which is transformed with the chimeric gene as defined in claim 11.

24. A plant which is transformed with the chimeric gene as defined in claim 12.

25. A plant which is transformed with the chimeric gene as defined in claim 13.

26. A plant which is transformed with the chimeric gene as defined in claim 14.

27. A plant which is transformed with the chimeric gene as defined in claim 15.

28. A plant which is transformed with the chimeric gene as defined in claim 16.

29. A plant which is transformed with the chimeric gene as defined in claim 17.

30. A method for changing a content of raffinose family oligosaccharides in a plant, comprising the steps of transforming the plant with the chimeric nucleic acid as defined in claim 6, and expressing the nucleic acid in cells of the plant.

31. A method for changing a content of raffinose family oligosaccharides in a plant, comprising the steps of transforming the plant with the chimeric nucleic acid as defined in claim 7, and expressing the nucleic acid in cells of the plant.

32. A method for changing a content of raffinose family oligosaccharides in a plant, comprising the steps of transforming the plant with the chimeric nucleic acid as defined in claim 8, and expressing the nucleic acid in cells of the plant.

33. A method for changing a content of raffinose family oligosaccharides in a plant, comprising the steps of transforming the plant with the chimeric nucleic acid as defined in claim 9, and expressing the nucleic acid in cells of the plant.

34. A method for changing a content of raffinose family oligosaccharides in a plant, comprising the steps of transforming the plant with the chimeric nucleic acid as defined in claim 10, and expressing the nucleic acid in cells of the plant.

35. A method for changing a content of raffinose family oligosaccharides in a plant, comprising the steps of transforming the plant with the chimeric nucleic acid as defined in claim 11, and expressing the nucleic acid in cells of the plant.

36. A method for changing a content of raffinose family oligosaccharides in a plant, comprising the steps of transforming the plant with the chimeric nucleic acid as defined in claim 12, and expressing the nucleic acid in cells of the plant.

37. A method for changing a content of raffinose family oligosaccharides in a plant, comprising the steps of transforming the plant with the chimeric nucleic acid as defined in claim 13, and expressing the nucleic acid in cells of the plant.

38. A method for changing a content of raffinose family oligosaccharides in a plant, comprising the steps of transforming the plant with the chimeric nucleic acid as defined in claim 14, and expressing the nucleic acid in cells of the plant.

39. A method for changing a content of raffinose family oligosaccharides in a plant, comprising the steps of transforming the plant with the chimeric nucleic acid as defined in claim 15, and expressing the nucleic acid in cells of the plant.

40. A method for changing a content of raffinose family oligosaccharides in a plant, comprising the steps of transforming the plant with the chimeric nucleic acid as defined in claim 16, and expressing the nucleic acid in cells of the plant.

41. A method for changing a content of raffinose family oligosaccharides in a plant, comprising the steps of transforming the plant with the chimeric nucleic acid as defined in claim 17, and expressing the nucleic acid in cells of the plant.

* * * * *

UNITED STATES PATENT AND TRADEMARK OFFICE
CERTIFICATE OF CORRECTION

PATENT NO. : 6,166,292
DATED : December 26, 2000
INVENTOR(S) : Chieko Osumi et al.

It is certified that error appears in the above-identified patent and that said Letters Patent is hereby corrected as shown below:

Title page,
Delete item [54] in its entirety and replace with --
[54] RAFFINOSE SYNTHASE GENE, METHOD FOR PRODUCING RAFFINOSE, AND TRANSGENIC PLANT --.

Column 45,
Lines 31-32, "57 to 2408" should read -- 56 to 2407 --;
Line 37, "57 to 2408" should read -- 56 to 2407 --;
Lines 60-61, "57 to 2408" should read -- 56 to 2407 --;
Line 66, "57 to 2408" should read -- 56 to 2407 --.

Signed and Sealed this

Twenty-third Day of October, 2001

Attest:

NICHOLAS P. GODICI
Acting Director of the United States Patent and Trademark Office Attesting Officer

UNITED STATES PATENT AND TRADEMARK OFFICE
CERTIFICATE OF CORRECTION

PATENT NO. : 6,166,292
DATED : December 26, 2000
INVENTOR(S) : Chieko Osumi et al.

It is certified that error appears in the above-identified patent and that said Letters Patent is hereby corrected as shown below:

Column 45,
Line 6, "57 to 2408" should read -- 56 to 2407 --; and
Line 11, "57 to 2408" should read -- 56 to 2407 --.

Signed and Sealed this

Twenty-third Day of April, 2002

Attest:

Attesting Officer

JAMES E. ROGAN
Director of the United States Patent and Trademark Office